US009167985B2

(12) United States Patent
Lovetri et al.

(10) Patent No.: US 9,167,985 B2
(45) Date of Patent: Oct. 27, 2015

(54) MICROWAVE TOMOGRAPHY SYSTEMS AND METHODS

(75) Inventors: Joe Lovetri, Winnipeg (CA); Puyan Mojabi, Winnipeg (CA)

(73) Assignee: UNIVERSITY OF MANITOBA, Winnipeg, Manitoba (CA)

(*) Notice: Subject to any disclaimer, the term of this patent is extended or adjusted under 35 U.S.C. 154(b) by 1192 days.

(21) Appl. No.: 13/051,267

(22) Filed: Mar. 18, 2011

(65) Prior Publication Data

US 2011/0227586 A1    Sep. 22, 2011

Related U.S. Application Data

(60) Provisional application No. 61/315,707, filed on Mar. 19, 2010.

(51) Int. Cl.
*A61B 5/00* (2006.01)
*A61B 5/053* (2006.01)
*A61B 5/05* (2006.01)

(52) U.S. Cl.
CPC ............ *A61B 5/0536* (2013.01); *A61B 5/0507* (2013.01)

(58) Field of Classification Search
CPC ........................... A61B 5/0536; A61B 5/0507
See application file for complete search history.

(56) References Cited

U.S. PATENT DOCUMENTS

| | | |
|---|---|---|
| 5,715,819 A | 2/1998 | Svenson et al. |
| 5,841,288 A | 11/1998 | Meaney et al. |
| 2006/0109010 A1* | 5/2006 | Edvardsson .................. 324/644 |
| 2006/0239404 A1* | 10/2006 | Udpa et al. ....................... 378/62 |
| 2006/0293597 A1* | 12/2006 | Johnson et al. ................ 600/437 |
| 2007/0015993 A1* | 1/2007 | Ciocan et al. .................. 600/407 |
| 2011/0137381 A1* | 6/2011 | Lee et al. ......................... 607/62 |
| 2012/0191148 A1* | 7/2012 | McKenna et al. ................. 607/3 |

FOREIGN PATENT DOCUMENTS

WO    WO 2009/066186 A2    5/2009
WO    WO 2009/066186 A3    7/2009

OTHER PUBLICATIONS

Abubakar et al., "Imaging of Biomedical Data Using a Multiplicative Regularized Contrast Source Inversion Method," *IEEE Trans. Microwave Theory Tech.*, Jul. 2002; 50(7): 1761-1771.
Abubakar et al. "The contrast source inversion method for location and shape reconstructions," 2002. *Inverse Problems*. 18:495-510.
Abubakar et al., "A robust iterative method for Born inversion," *IEEE Trans. Geosci. Remote Sensing*, Feb. 2004; 42(2): 342-354.
Abubakar et al., "Iterative forward and inverse algorithms based on domain integral equations for three-dimensional electric and magnetic objects," *J. Comput. Phys.*, Mar. 20, 2004; 195(1): 236-262. Available online Nov. 18, 2003.
Abubakar et al., "A multiplicative regularization approach for deblurring problems," *IEEE Trans. Image Process.*, Nov. 2004; 13(11): 1524-1532.
Abubakar et al., "2.5D forward and inverse modeling for interpreting low-frequency electromagnetic measurements," *Geophysics*, Jul. 1, 2008; 73(4): F165-177.

(Continued)

*Primary Examiner* — Jeff Natalini
(74) *Attorney, Agent, or Firm* — Mueting Raasch & Gebhardt, P.A.

(57) ABSTRACT

Methods and/or systems are disclosed herein for use in imaging an object with microwave tomography using a plurality of different boundary conditions.

20 Claims, 13 Drawing Sheets

(56) References Cited

OTHER PUBLICATIONS

Broquetas et al., "Cylindrical geometry: a further step in active microwave tomography," *IEEE Trans. Microwave Theory Tech.*, May 1991; 39(5): 836-844.

Bulyshev et al., "Three dimensional microwave tomography. Theory and computer experiments in scalar approximation," *Inverse Problems*, Jun. 2000; 16(3): 863-875.

Charbonnier et al., "Deterministic Edge-Preserving Regularization in Computed Imaging," *IEEE Trans. on Image Processing*, Feb. 1997; 6(2): 298-311.

Chew et al., "Reconstruction of Two-Dimensional Permittivity Distribution Using the Distorted Born Iterative Method," *IEEE Trans. Med. Imaging*, Jun. 1990; 9(2): 218-225.

Crocco et al., "On embedded microwave imaging systems: retrievable information and design guidelines," *Inverse Problems*, Mar. 27, 2009; 25(6): 065001 (17 pgs).

Fhager et al., "Reconstruction quality and spectral content of an electromagnetic time-domain inversion algorithm," *IEEE Trans. Biomed. Eng.*, Aug. 2006; 53(8): 1594-1604.

Franchois et al., "Quantitative microwave imaging with a 2.45-GHz planar microwave camera," *IEEE Trans. Med. Imaging*, Aug. 1998; 17(4): 550-561.

Franchois et al., "A quasi-Newton reconstruction algorithm for a complex microwave imaging scanner environment," *Radio Sci.*, Jan. 10, 2003; 38(2): 8011-8023.

Franza et al., "SICS: A sensor interaction compensation scheme for microwave imaging," *IEEE Trans. Antennas Propag.*, Feb. 2002; 50(2): 211-216.

Gilmore et al., "Enhancement of microwave tomography through the use of electrically conducting enclosures," *Inverse Problems*, Apr. 8, 2008; 24(3): 035008 (21 pgs).

Gilmore et al., "Microwave Biomedical Data Inversion Using the Finite-Difference Contrast Source Inversion Method," *IEEE Trans. Antennas Propag.*, May 2009; 57(5): 1528-1538.

Gilmore et al., "A wideband microwave tomography system with a novel frequency selection procedure," *IEEE Transaction on Biomed Eng.*, Apr. 2010; 57(4): 894-904. Available online Nov. 20, 2009.

Gilmore et al., "Corrections to the 'Enhancement of microwave tomography through the use of electrically conducting enclosures,'" *Inverse Problems*, Jan. 2010; 26(1): 019801 (7 pgs.).

Gilmore et al., "On Super-Resolution With an Experimental Microwave Tomography System," *IEEE Antennas and Wireless Propagation Letters*; May 3, 2010; 9: 393-396.

Habashy et al., "A general framework for constraint minimization for the inversion of electromagnetic measurements," *Progress in Electromagnetics Research*, 2004; 46: 265-312.

Lazebnik et al., "Highly Accurate Debye Models for Normal and Malignant Breast Tissue Dielectric Properties at Microwave Frequencies," *IEEE Microwave and Wireless Components Letters*, Dec. 2007; 17(12): 822-824.

Lencrerot et al., "Imposing Zernike representation for imaging two-dimensional targets," *Inverse Problems in Science and Engineering*, Feb. 3, 2009; 25(3): 035012 (21 pgs).

Lencrerot et al., "Measurement strategies for a confined microwave circular scanner," *Inverse Problems in Science and Engineering*, Sep. 2009; 17(6): 787-802. Available online Aug. 6, 2009.

LoVetri, "Computational electromagnetics and electromagnetic inverse imaging," Grant Abstract [online]. Natural Sciences and Engineering Research Council of Canada, project dates: fiscal year 2010-2011 [retrieved on Aug. 9, 2011]. Retrieved from the Internet: <URL: http://www.outil.ost.uqam.ca/CRSNG/Detail.aspx?Cle=451511&Langue=2>, 2 pgs.

Enclosed Meaney et al., "Microwave imaging for tissue assessment: initial evaluation in multitarget tissue-equivalent phantoms," *IEEE Trans. Biomed Eng.*, Sep. 1996; 43(9): 878-890.

Meaney et al., "Nonactive antenna compensation for fixed-array microwave imaging: Part II—Imaging results," *IEEE Trans. Med. Imaging*, Jun. 1999; 18(6): 508-518.

Meaney et al., "A clinical prototype for active microwave imaging of the breast," *IEEE Trans. Microwave Theory Tech.*, Nov. 2000; 48(11): 1841-1853.

Meaney et al., "Pre-scaled two-parameter Gauss-Newton image reconstruction to.reduce property recovery imbalance," *Phys. Med. Biol.*, Apr. 7, 2002; 47(7): 1101-1119.

Meaney et al., "Initial clinical experience with microwave breast imaging in women with normal mammography," *Acad Radiol.*, Feb. 2007; 14(2): 207-218.

Mojabi et al., "Adapting the Normalized Cumulative Periodogram Parameter-Choice Method to the Tikhonov Regularization of 2-D/TM Electromagnetic Inverse Scattering Using Born Iterative Method," *Progress in Electromagnetics Research M*, 2008; 1: 111-138.

Mojabi et al., "Preliminary Investigation of the NCP Parameter-Choice Method.For Inverse Scattering Problems Using BIM: 2-D TM Case," *Appl. Comp. Electromag. Soc.*, Sep. 2008; 23(3): 207-214.

Mojabi et al., "Biomedical microwave inversion in conducting cylinders of arbitrary shapes," *13th International Symposium on Antenna Technology and Applied Electromagnetics and the Canadian Radio Science Meeting (ANTEM/URSI)*, Toronto, Ontario, Feb. 15-18, 2009: 1-4.

Mojabi et al., "Microwave Biomedical Imaging Using the Multiplicative Regularized Gauss—Newton Inversion," *IEEE Antennas and Wireless Propagation Letters*, May 26, 2009; 8: 645-648.

Mojabi et al., "Overview and Classification of Some Regularization Techniques for the Gauss-Newton Inversion Method Applied to Inverse Scattering Problems," *IEEE Trans. Antennas Propag.*, Sep. 2009; 57(9): 2658-2665. Available online Jul. 10, 2009.

Mojabi et al., "Enhancement of the Krylov subspace regularization for microwave biomedical imaging," *IEEE Trans. Med Imaging*, Dec. 2009; 28(12): 2015-2019. Available online Jul. 24, 2009.

Mojabi et al., "Eigenfunction contrast source inversion for circular metallic enclosures," *Inverse Problems*, Feb. 2010; 26(2): 025010 (23 pgs.).

Mojabi et al., "Comparison of TE and TM Inversions in the Framework of the Gauss-Newton Method," *IEEE Trans. Antennas Propag.*, Apr. 2010; 58(4): 1336-1348.

Mojabi et al., "A Novel Microwave Tomography System Using a Rotatable Conductive Enclosure," *IEEE Transactions on Antennas and Propagation*, May 2, 2011; 59(5): 1597-1605. Available online Mar. 7, 2011.

O'Halloran et al., "Rotating Antenna Microwave Imaging System for Breast Cancer Detection," *Progress in Electromagnetics Research*, 2010; 107: 203-217.

Pastorino, "Stochastic Optimization Methods Applied to Microwave Imaging: A Review," *IEEE Trans. Antennas Propag.*, Mar. 2007; 55(3): 538-548.

Paulsen et al., "Nonactive antenna compensation for fixed-array microwave imaging—Part I: Model development," *IEEE Trans. Med. Imag.*, Jun. 1999; 18(6): 496-507.

Rubaek et al., "Nonlinear Microwave Imaging for Breast-Cancer Screening Using Gauss-Newton's Method and the CGLS Inversion Algorithm," *IEEE Trans. Antennas Propag.*, Aug. 2007; 55(8): 2320-2331.

Rubaek et al., "Computational Validation of a 3-D Microwave Imaging System for Breast-Cancer Screening," *IEEE Transactions Antennas and Propag.*, Jul. 2009; 57(7): 2105-2115.

Semenov et al., "Spatial resolution of microwave tomography for detection of myocardial ischemia and infarction-experimental study on two-dimensional models," *IEEE Trans. Microwave Theory Tech.*, Apr. 2000; 48(4): 538-544.

Semenov et al., "Three-dimensional microwave tomography: initial experimental imaging of animals," *IEEE Trans. Biomed. Eng.*, Jan. 2002; 49(1): 55-63.

Tijhuis et al., "Theoretical and Computational Aspects of 2-D Inverse Profiling," *IEEE Trans. Geosci. Remote Sensing*, Jun. 2001; 39(6): 1316-1330.

van den Berg et al. "A contrast source inversion method", 1997. *Inverse Problems.* 13:1607-1620.

(56) References Cited

OTHER PUBLICATIONS

Wadbro et al., "Microwave Tomography Using Topology Optimization Techniques," *SIAM J. Sci. Comput.*, Mar. 2008; 30(3): 1613-1633.

Wang et al., "An iterative solution of the two-dimensional electromagnetic inverse scattering problem," *Int. J. Imag. Syst. Technol.*, Sum. 1989;1(1): 100-108. Available online Oct. 20, 2005.

Yu et al., "Active Microwave Imaging II: 3-D System Prototype and Image Reconstruction From Experimental Data," *IEEE Trans. Microwave Theory Tech.*, Apr. 2008; 56(4): 991-1000.

Zaeytijd et al., "Full-Wave Three-Dimensional Microwave Imaging With a Regularized Gauss-Newton Method-Theory and Experiment," *IEEE Trans. Antennas Propag.*, Nov. 2007; 55(11): 3279-3292.

\* cited by examiner

Real($\varepsilon_r$)    Imaginary($\varepsilon_r$)

Real($\varepsilon_r$)    Imaginary($\varepsilon_r$)

Real($\varepsilon_r$)    Imaginary($\varepsilon_r$)

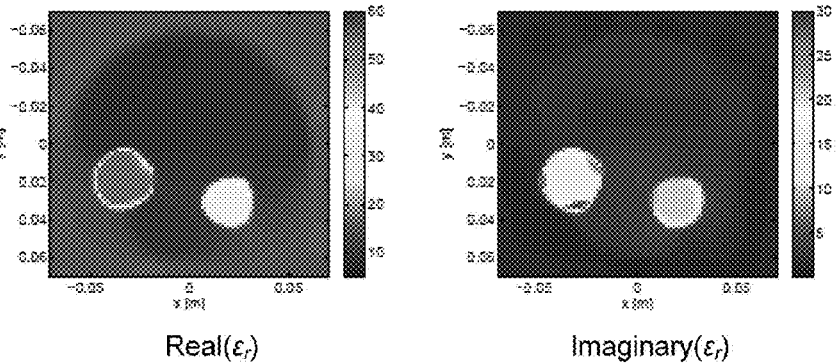
Fig. 8A    Real($\varepsilon_r$)    Imaginary($\varepsilon_r$)
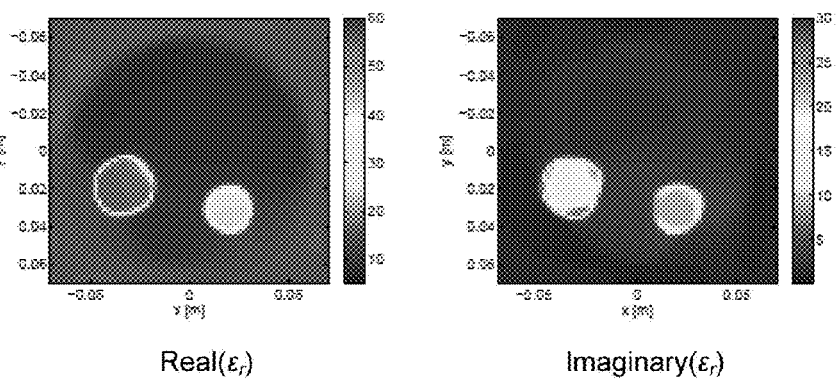
Fig. 8B    Real($\varepsilon_r$)    Imaginary($\varepsilon_r$)
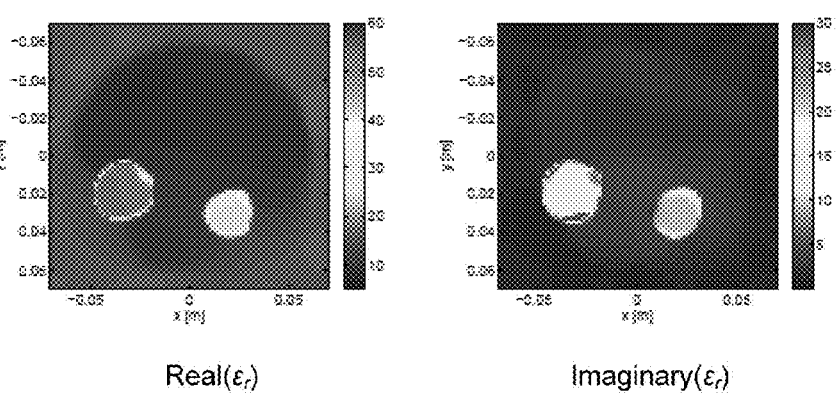
Fig. 8C    Real($\varepsilon_r$)    Imaginary($\varepsilon_r$)

Fig. 10
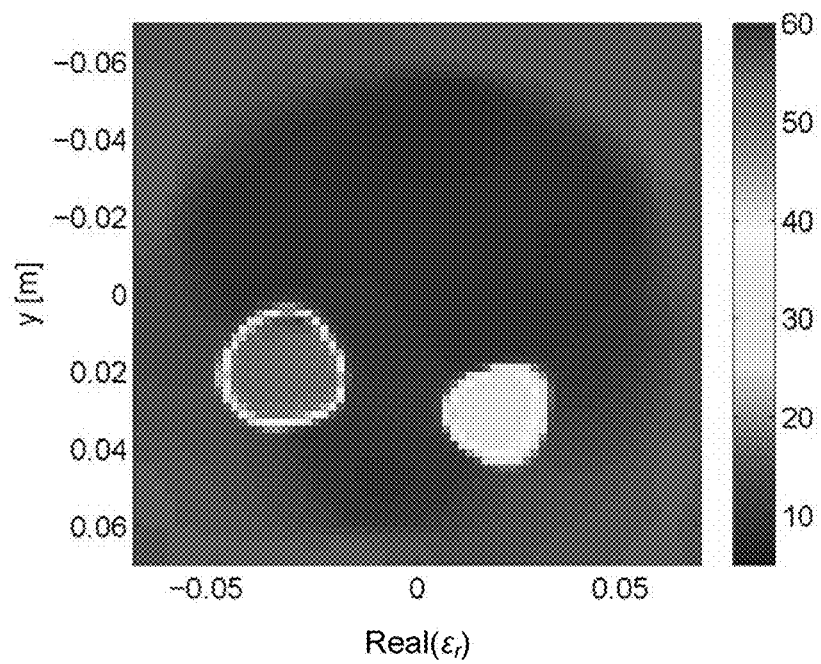
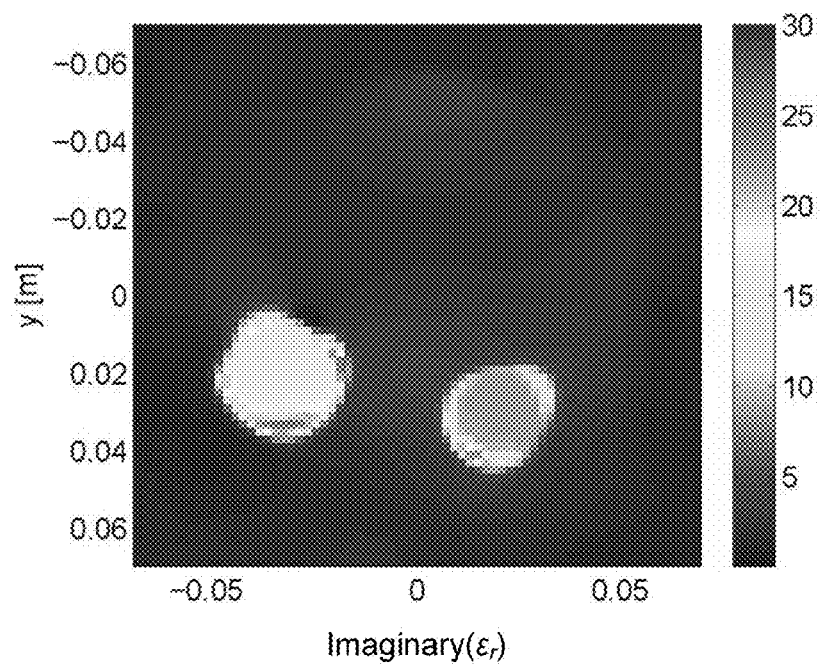

*Fig. 11*
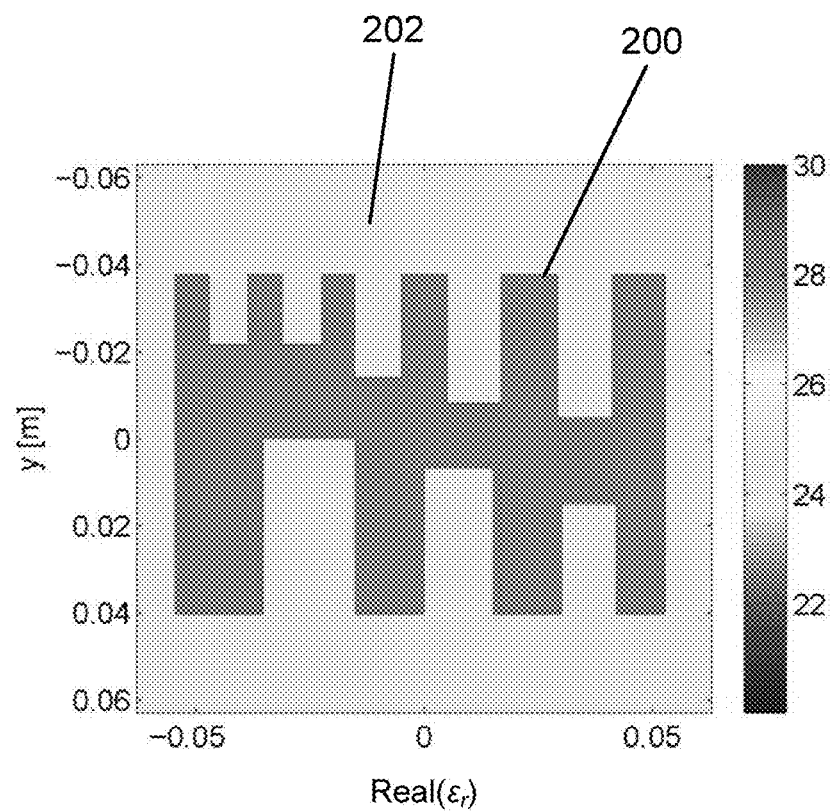
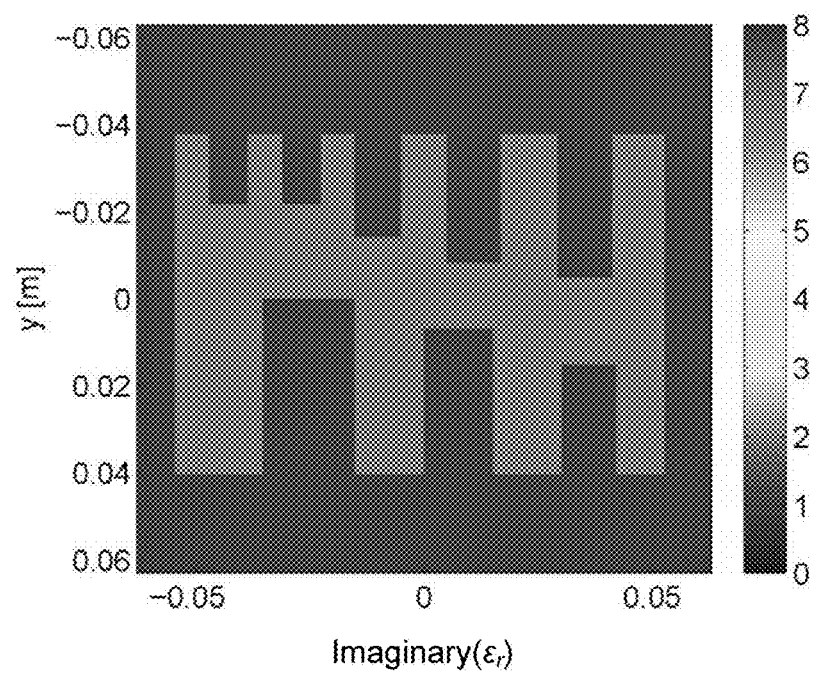

Real($\varepsilon_r$)  Imaginary($\varepsilon_r$)

Real($\varepsilon_r$)  Imaginary($\varepsilon_r$)

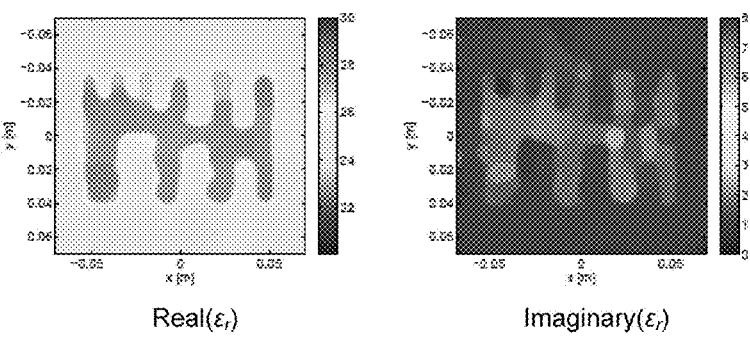
Fig. 13A  Real($\varepsilon_r$)   Imaginary($\varepsilon_r$)
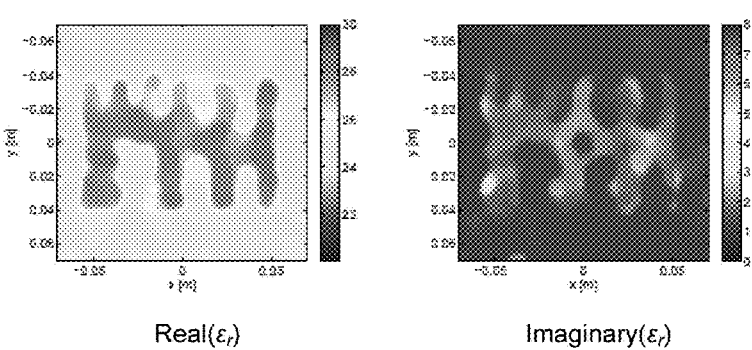
Fig. 13B  Real($\varepsilon_r$)   Imaginary($\varepsilon_r$)

MICROWAVE TOMOGRAPHY SYSTEMS AND METHODS

CROSS-REFERENCE TO RELATED APPLICATIONS

This application claims the benefit of U.S. Provisional Application Ser. No. 61/315,707 filed 19 Mar. 2010, entitled "Microwave Tomography Systems and Methods," which is incorporated herein by reference in its entirety.

BACKGROUND

The disclosure herein relates generally to microwave tomography. More particularly, the disclosure herein pertains to methods and systems of microwave tomography (MWT) for use in, e.g., imaging applications (e.g., tumor detection in human tissue, etc.).

Tomography is imaging by sections or sectioning to convey internal structures of an object, for example, the human body or the earth. Microwave tomography (MWT) systems irradiate an object of interest, or object to be imaged, with electromagnetic energy, measure or sample the resultant scattered electromagnetic energy, and generate or reconstruct an image of the object based on the resultant scattered electromagnetic energy. "Scattering" is a general physical process whereby some forms of radiation, such as light, sound, or moving particles, for example, are forced to deviate from a straight trajectory by one or more non-uniformities in a medium through which it passes. The "inverse problem" may be used to determine the characteristics of an object of interest such as its shape and internal constitution from the resultant scattered electromagnetic energy.

An exemplary tomography system, e.g., a microwave tomography system, is described in Patent Cooperation Treaty Patent Application Pub No. WO 2009/066186 A2 filed on Nov. 21, 2008 and entitled "System and Methods of Improved Tomography Imaging," which is incorporated herein by reference in its entirety.

Contributions to MWT have been made in all aspects of the technology, especially the development of improved inversion algorithms (see, e.g., T. Rubaek, P. M. Meaney, P. Meincke, and K. D. Paulsen, "Nonlinear microwave imaging for breast-cancer screening using Gauss-Newton's method and the CGLS inversion algorithm," IEEE Trans. Antennas Propag., vol. 55, no. 8, pp. 2320-2331, August 2007; A. Abubakar, P. M. van den Berg, and J. J. Mallorqui, "Imaging of biomedical data using a multiplicative regularized contrast source inversion method," IEEE Trans. Microwave Theory Tech., vol. 50, no. 7, pp. 1761-1777, July 2002; J. D. Zaeytijd, A. Franchois, C. Eyraud, and J.-M. Geffrin, "Full-wave three-dimensional microwave imaging with a regularized Gauss-Newton method-theory and experiment," IEEE Trans. Antennas Propag., vol. 55, no. 11, pp. 3279-3292, November 2007; and W. C. Chew and Y. M. Wang, "Reconstruction of two-dimensional permittivity distribution using the distorted Born iterative method," IEEE Trans. Med. Imaging, vol. 9, no. 2, pp. 218-225, 1990).

Further, diverse antenna or transducer systems have been utilized in the actual physical setups used to collect electromagnetic scattering data in MWT systems (see, e.g., P. Meaney, M. Fanning, D. Li, S. Poplack, and K. Paulsen, "A clinical prototype for active microwave imaging of the breast," IEEE Trans. Microwave Theory Tech., vol. 48, no. 11, pp. 1841-1853, November 2000; A. Franchois, A. Joisel, C. Pichot, and J.-C. Bolomey, "Quantitative microwave imaging with a 2.45-GHz planar microwave camera," IEEE Trans. Med. Imag., vol. 17, no. 4, pp. 550-561, August 1998; A. Broquetas, J. Romeu, J. Rius, A. Elias-Fuste, A. Cardama, and L. Jofre, "Cylindrical geometry: a further step in active microwave tomography," IEEE Trans. Microwave Theory Tech., vol. 39, no. 5, pp. 836-844, May 1991; S. Y. Semenov, R. H. Svenson, A. E. Bulyshev, A. E. Souvorov, A. G. Nazarov, Y. E. Sizov, V. G. Posukh, A. Pavlovsky, P. N. Repin, A. N. Starostin, B. A. Voinov, M. Taran, G. P. Tastis, and V. Y. Baranov, "Three-dimensional microwave tomography: Initial experimental imaging of animals," IEEE Trans. Biomed. Eng., vol. 49, no. 1, pp. 55-63, January 2002; A. Fhager, P. Hashemzadeh, and M. Persson, "Reconstruction quality and spectral content of an electromagnetic time-domain inversion algorithm," IEEE Trans. Biomed. Eng., vol. 53, no. 8, pp. 1594-1604, August 2006; C. Yu, M. Yuan, J. Stang, E. Bresslour, R. George, G. Ybarra, W. Joines, and Q. H. Liu, "Active microwave imaging II: 3-D system prototype and image reconstruction from experimental data," IEEE Trans. Microwave Theory Tech., vol. 56, no. 4, pp. 991-1000, April 2008; T. Rubaek, O. Kim, and P. Meincke, "Computational validation of a 3D microwave imaging system for breast-cancer screening," IEEE Trans. Antennas Propag., vol. 57, no. 7, pp. 2105-2115, July 2009; and A. E. Bulyshev, A. E. Souvorov, S. Y. Semenov, R. H. Svenson, A. G. Nazarov, Y. E. Sizov, and G. P. Tastis, "Three dimensional microwave tomography theory and computer experiments in scalar approximation," Inverse Probl., vol. 16, pp. 863-875, 2000).

In many previous MWT systems, the object of interest and the antennas are contained within a chamber, usually made from a dielectric material, such as plexiglass. The dielectric chamber is usually filled with a lossy matching fluid, e.g., a 87:13 glycerin:water solution (see, e.g., T. Rubaek, P. M. Meaney, P. Meincke, and K. D. Paulsen, "Nonlinear microwave imaging for breast-cancer screening using Gauss-Newton's method and the CGLS inversion algorithm," IEEE Trans. Antennas Propag., vol. 55, no. 8, pp. 2320-2331, August 2007; and P. M. Meaney, M. W. Fanning, T. Raynolds, C. J. Fox., Q. Fang, C. A. Kogel, S. P. Poplack, and K. D. Paulsen, "Initial clinical experience with microwave breast imaging in women with normal mammography," Acad Radiol., March 2007).

Further, in one or more previous MWT systems, the object of interest and the antennas have been enclosed by a circular metallic enclosure (see, e.g., L. Crocco and A. Litman, "On embedded microwave imaging systems: retrievable information and design guidelines," Inverse Problems, vol. 25, no. 6, 2009, 065001 (17 pp); C. Gilmore and J. LoVetri, "Enhancement of microwave tomography through the use of electrically conducting enclosures," Inverse Problems, vol. 24, no. 3, 2008, 035008 (21 pp); A. Franchois and A. G. Tijhuis, "A quasi-Newton reconstruction algorithm for a complex microwave imaging scanner environment," Radio Sci., vol. 38, no. 2, 2003; R. Lencrerot, A. Litman, H. Tortel, and J.-M. Geffrin, "Measurement strategies for a confined microwave circular scanner," Inverse Problems in Science and Engineering, pp. 1-16, January 2009; "Imposing Zernike representation for imaging two-dimensional targets," Inverse Problems, vol. 25, no. 3, 2009, 035012 (21 pp); and P. Mojabi and J. LoVetri, "Eigenfunction contrast source inversion for circular metallic enclosures," Inverse Problems, vol. 26, no. 2, February 2010, 025010 (23 pp)). Still further, in previous MWT systems, the object of interest and the antennas have been enclosed in conducting cylinders of arbitrary shapes (see, e.g., P. Mojabi, C. Gilmore, A. Zakaria, and J. LoVetri, "Biomedical microwave inversion in conducting cylinders of arbitrary shapes," in 13th International Symposium on Antenna Technology and Applied Electromagnetics and the Canadian Radio Science Meeting (ANTEM/URSI), February 2009, pp. 1-4).

Obtaining quality images using MWT may require accurate collection of a substantial amount of electromagnetic scattering data, which may often be performed using a relatively large number of co-resident antennas. For example, many present MWT systems include antenna arrays that range from 16 to 32 elements in which small monopoles or Vivaldi antennas have been used. These large antenna arrays may facilitate gathering of bistatic scattering data at many angles without mechanically repositioning the antennas. The antenna elements themselves are not typically taken fully into account in the electromagnetic system model of the associated nonlinear optimization problem, although it may be a consideration in achieving good images (compare, e.g., the antenna compensation schemes in the following: K. Paulsen and P. Meaney, "Nonactive antenna compensation for fixed-array microwave imaging. I. Model development," IEEE Trans. Med. Imag., vol. 18, no. 6, pp. 496-507, June 1999; P. Meaney, K. Paulsen, J. Chang, M. Fanning, and A. Hartov, "Nonactive antenna compensation for fixed-array microwave imaging. II. Imaging results," IEEE Trans. Med. Imag., vol. 18, no. 6, pp. 508-518, June 1999; and O. Franza, N. Joachimowicz, and J.-C. Bolomey, "SICS: A sensor interaction compensation scheme for microwave imaging," IEEE Trans. Antennas Propag., vol. 50, no. 2, pp. 211-216, February 2002).

Including the antennas in the MWT system model may be one way of reducing modeling error that exists between a numerical system model, used in an inversion algorithm, and the actual system, from which data is collected. Modeling error may also occur when assuming a homogeneous unbounded domain for the numerical system model (i.e., assuming that the matching fluid extends to infinity) because the boundary conditions for the dielectric discontinuity, e.g., at a MWT system's dielectric casing (e.g., a plexiglass casing), may actually be required to properly account for the finite extent of the matching-fluid region. Both the antenna and the boundary condition modeling errors may be reduced by using lossy matching fluid of sufficiently high loss such that electromagnetic energy returning from the boundary, or any passive antenna, to any receiving antenna is not appreciable. Although the use of a lossy matching fluid may reduce modeling errors, the net effect of using a lossy matching fluid in MWT systems may also be to reduce the accuracy of the complex permittivity profile reconstructions because the addition of any loss reduces the dynamic range and achievable signal-to-noise ratio of the system.

A MWT system that uses a rotating metallic hexagonal-shaped container where the object of interest is illuminated by waveguides (e.g., each of the waveguides acts as both a transmitter and a receiver) connected, or fixedly attached, to each side of the metallic container has been previously described (see, e.g., E. Wadbro and M. Berggren, "Microwave tomography using topology optimization techniques," SIAM J. Sci. Comput., vol. 30, no. 3, pp. 1613-1633, 2008). In this system, a container, along with the attached waveguides, may be rotated about the object of interest to collect additional scattering data, and topology optimization techniques may be used to invert the data. At each rotation, however, this system produces an identical incident field with respect to the boundary (i.e., the boundary condition) of the enclosure because the microwave sources (i.e., the waveguides) remain fixed with respect to the boundary. In other words, this system produces identical boundary conditions with respect to its waveguides (i.e., its transmitters and receivers) because the waveguides are fixedly attached to the enclosure, and therefore, rotate with the enclosure.

SUMMARY

The disclosure herein relates to MWT methods and systems that use scattering data collected within a plurality of different boundary conditions to reconstruct an image of an object of interest. For example, the object of interest may be irradiated with electromagnetic energy within two or more different boundary conditions thereby providing two or more unique sets of resultant scattering data from which an image of the object may be constructed.

In at least one exemplary method of imaging an object using microwave tomography, the exemplary method includes providing one or more antennas (e.g., less than eight antennas) positioned relative to an object and providing boundary condition apparatus configured to present a plurality of different boundary conditions (e.g., at least three different boundary conditions) relative to the one or more antennas. The exemplary method further includes delivering electromagnetic energy using at least one of the one or more antennas to irradiate the object resulting in scattered electromagnetic energy for each of the plurality of different boundary conditions presented by the boundary condition apparatus (e.g., delivering electromagnetic energy with each of the one or more antennas individually until each antenna has individually delivered electromagnetic energy to irradiate the object for each of the plurality of different boundary conditions), sampling the scattered electromagnetic energy using at least one of the one or more antennas for each of the plurality of different boundary conditions, and reconstructing an image of the object based on the sampled scattered electromagnetic energy.

In one or more exemplary methods and systems described herein, each antenna of the one or more antennas may be in a fixed position relative to the object and/or at least one antenna of the one or more antennas may be attached to the object.

Further, in one or more exemplary methods and systems described herein, the boundary condition apparatus may include a conductive enclosure (e.g., a triangular enclosure) and the exemplary methods may further include positioning the object within the conductive enclosure. Also, in at least one embodiment, the boundary condition apparatus may present each of the different boundary conditions by changing the orientation of the enclosure (e.g., rotating the enclosure) relative to the object and the one or more antennas.

Still further, in one or more exemplary methods described herein, the exemplary method may further include surrounding the object with a low-loss fluid.

In at least one exemplary system for use in imaging an object, the exemplary system includes one or more antennas positionable relative to an object to be imaged and boundary condition apparatus configured to present a plurality of different boundary conditions relative to the one or more antennas. In this exemplary system, the one or more antennas may be configured to deliver electromagnetic energy to irradiate an object to be imaged resulting in scattered electromagnetic energy for each of the plurality of different boundary conditions, and the one or more antennas may be further configured to sample the scattered electromagnetic energy for each of the plurality of different boundary conditions. The exemplary system further includes processing apparatus configured to reconstruct an image of an object based on the sampled scattered electromagnetic energy.

In one or more embodiments, the one or more antennas are configured to deliver electromagnetic energy with each of the one or more antennas individually until each antenna has individually delivered electromagnetic energy to irradiate the object for each of the plurality of different boundary conditions. Further, in one or more embodiments, the boundary condition apparatus may be further configured to surround the object with a low-loss fluid.

In at least another exemplary method of imaging an object using microwave tomography, the exemplary method includes providing one or more antennas positioned relative to an object to be imaged (e.g., where each of the one or more antennas is in a fixed position relative to the object), presenting a plurality of different boundary conditions relative to the object being imaged and the one or more antennas, and delivering electromagnetic energy using at least one of the one or more antennas to irradiate the object resulting in scattered electromagnetic energy for each of the plurality of different boundary conditions. The exemplary method further includes sampling the scattered electromagnetic energy using at least one of the one or more antennas and reconstructing an image of the object based on the sampled scattered electromagnetic energy.

In at least another exemplary system, the exemplary system may include a rotatable, conductive enclosure within which transmitters generate electromagnetic scattering data that is collected at multiple static positions within the enclosure using a minimal antenna array having, e.g., as few as four co-resident elements. The antenna array may remain fixed with respect to the object being imaged and the boundary of the conductive enclosure may be rotated with respect to the antenna array. In at least one embodiment, scattered-field data may be obtained by taking bistatic measurements between each pair of elements of the fixed array at several different static positions of the rotatable enclosure.

In one or more exemplary methods and/or systems described herein, the exemplary methods and/or systems may use the inverse problem to construct images of the electrical properties of an object of interest. The inverse problem may be formulated for a two-dimensional (2D) Transverse Magnetic (TM) case and an enclosed-triangle boundary condition. In this exemplary system, antenna modeling error may be minimized because small arrays with as few as four elements may be used. Further, a triangular-shaped enclosure (to provide the enclosed-triangle boundary condition) is the polygon that allows the greatest number of fixed-angle, step-rotations (i.e., rotation about an axis perpendicular to the triangular cross-section) before producing a redundant configuration (or redundant boundary condition).

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

FIG. 8A provides exemplary images of the object of interest of FIG. 3 reconstructed using scattered electromagnetic energy collected in a simulated MWT system using sixteen antennas and the boundary conditions of FIG. 4A & FIG. 4B.

FIG. 8B provides exemplary images of the object of interest of FIG. 3 reconstructed using scattered electromagnetic energy collected in a simulated MWT system using sixteen antennas and the boundary conditions of FIG. 4A & FIG. 4C.

FIG. 8C provides exemplary images of the object of interest of FIG. 3 reconstructed using scattered electromagnetic energy collected in a simulated MWT system using sixteen antennas and the boundary conditions of FIG. 4B & FIG. 4C.

FIG. 10 provides exemplary images of the object of interest of FIG. 3 reconstructed using scattered electromagnetic energy collected in a simulated MWT system using four antennas and the rotatable, triangular enclosure of FIG. 9.

FIG. 11 provides another exemplary simulated object of interest, e.g., to be imaged by the systems and/or methods described herein.

FIGS. 13A-B provide exemplary enhanced images of the images of FIGS. 12A-B, respectively.

DETAILED DESCRIPTION OF EXEMPLARY EMBODIMENTS

Figure 1:
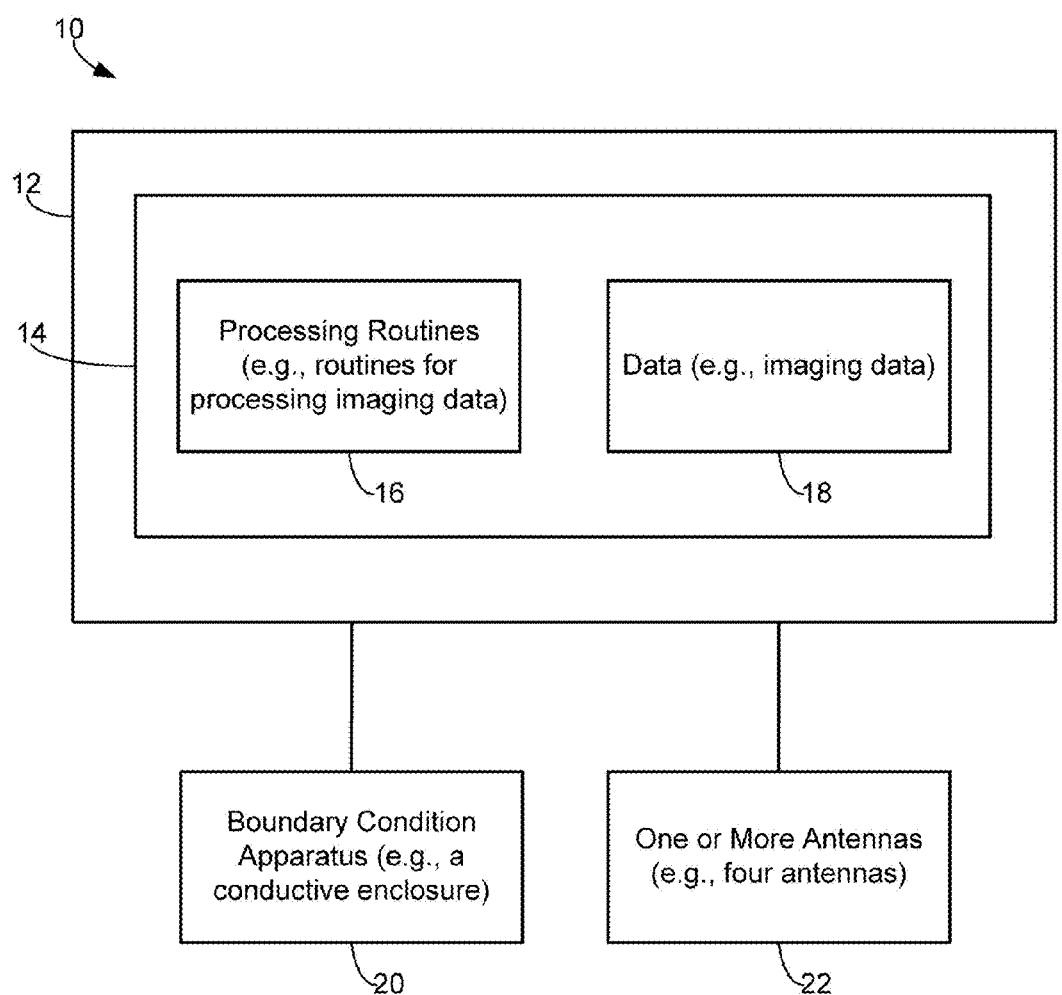
FIG. 1 is a block diagram depicting an exemplary microwave tomography imaging system.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods, apparatus, and systems shall be described with reference to FIGS. 1-13. It will be apparent to one skilled in the art that elements or processes from one embodiment may be used in combination with elements or processes of the other embodiments, and that the possible embodiments of such methods, apparatus, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

FIG. 1 shows an exemplary imaging system 10 (e.g., a MWT imaging system) including processing apparatus (block 12), boundary condition apparatus (block 20), and one or more antennas (block 22). The processing apparatus (block 12) may be operably coupled to the boundary condition apparatus (block 20) and the one or more antennas (block 22) to facilitate imaging of an object of interest using the boundary condition apparatus (block 20) and the one or more antennas (block 22). Further, the processing apparatus (block 12) includes data storage (block 14). Data storage (block 14) allows for access to processing programs or routines (block 16) and one or more other types of data (block 18) that may be employed to carry out the exemplary imaging methods (e.g., one which is shown generally in the block diagram of FIG. 2).

For example, processing programs or routines (block 16) may include programs or routines for performing computational mathematics, matrix mathematics, compression algorithms (e.g., data compression algorithms), calibration algorithms, image construction algorithms, inversion algorithms, signal processing algorithms, standardization algorithms, comparison algorithms, vector mathematics, or any other processing required to implement one or more embodiments as described herein. Exemplary mathematical formulations/equations that may be used in the MWT tomography systems and methods described herein are more specifically described herein with reference to FIGS. 3-13.

Data (block 18) may include, for example, sampled electromagnetic energy (e.g., sampled or collected using the one or more antennas (block 22)), data representative of measurements (e.g., electromagnetic scattering data), results from one or more processing programs or routines employed according to the disclosure herein (e.g., reconstructed images of an object of interest), or any other data that may be necessary for carrying out the one or more processes or methods described herein.

In one or more embodiments, the system 10 may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or processes as described herein or as would be applied in a known fashion.

The program used to implement the processes described herein may be provided using any programmable language, e.g., a high level procedural and/or object orientated programming language that is suitable for communicating with a computer system. Any such programs may, for example, be stored on any suitable device, e.g., a storage media, readable by a general or special purpose program, computer or a processor apparatus for configuring and operating the computer when the suitable device is read for performing the procedures described herein. In other words, at least in one embodiment, the system 10 may be implemented using a computer readable storage medium, configured with a computer program, where the storage medium so configured causes the computer to operate in a specific and predefined manner to perform functions described herein.

Likewise, the imaging system 10 may be configured at a remote site (e.g., application server) that allows access by one or more users via a remote computer apparatus (e.g., via a web browser), and allows a user to employ the functionality according to the present disclosure (e.g., user accesses a graphical user interface associated with one or more programs to process data).

The processing apparatus (block 12), may be, for example, any fixed or mobile computer system (e.g., a personal computer or mini computer). The exact configuration of the computing apparatus is not limiting and essentially any device capable of providing suitable computing capabilities and control capabilities (e.g., control the imaging set up configuration and acquire data, such as electromagnetic scattering data) may be used. Further, various peripheral devices, such as a computer display, mouse, keyboard, memory, printer, scanner, etc. are contemplated to be used in combination with the processing apparatus (block 12).

Further, in one or more embodiments, the output (e.g., an image, image data, an image data file, a digital file, a file in user-readable format, etc.) may be analyzed by a user, used by another machine that provides output based thereon, etc.

As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by processing apparatus (block 14) described herein.

Also, as described herein, a file in user-readable format may be any representation of data (e.g., ASCII text, binary numbers, hexadecimal numbers, decimal numbers, audio, graphical) presentable on any medium (e.g., paper, a display, sound waves, etc.) readable and/or understandable by a user.

Generally, the methods and systems as described herein may utilize algorithms implementing computational mathematics (e.g., matrix inversions, substitutions, Fourier transform techniques, etc.) to reconstruct the images described herein (e.g., from sampled electromagnetic scattering data).

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

One will recognize that a graphical user interface may be used in conjunction with the embodiments described herein. The user interface may provide various features allowing for user input thereto, change of input, importation or exportation of files, or any other features that may be generally suitable for use with the processes described herein. For example, the user interface may allow default values to be used or may require entry of certain values, limits, threshold values, or other pertinent information.

The methods described in this disclosure, including those attributed to the systems, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, image processing devices, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems, devices and methods described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

The imaging system 10 further includes boundary condition apparatus (block 20) and one or more antennas (block 22). Generally, the boundary condition apparatus (block 20) and the one or more antennas (block 22) are configured to be utilized together to provide a plurality of different incident fields (e.g., fields incident on an object of interest) resulting in a plurality of different scattered fields, to sample or collect data from the resultant scattered fields, and to provide the resultant, scattered-field data to the processing apparatus (block 12) such that an image may be constructed based on such data.

The boundary condition apparatus (block 20) may be any apparatus configurable to present at least two, or a plurality of, different boundary conditions relative to the one or more antennas (block 22). Each different boundary condition presented by the boundary condition apparatus (block 22) may provide a unique or different incident field resulting in a unique or different scattered field to sample.

Exemplary boundary condition apparatus (block 20) may include a conductive enclosure and/or one or more conductive walls configured to provide the plurality of different boundary conditions relative to the one or more antennas (block 22). The plurality of different boundary conditions providable by the boundary condition apparatus (block 20) may include an open-region boundary condition, one or more enclosed-region boundary conditions, and one or more partially-enclosed-region boundary conditions.

The open-region boundary condition may be, for example, a boundary condition that is assumed to extend to infinity. For example, the boundary condition apparatus (block 20) may be a conductive enclosure that is moveable away from one or more antennas (block 22) to provide the open-region boundary condition.

An enclosed-region boundary condition may be, for example, a boundary condition that is a known, finite boundary. For example, the boundary condition apparatus (block 20) may be a conductive enclosure that surrounds the object of interest.

A partially-enclosed boundary condition may be, for example, a boundary condition that is partially-open and also partially enclosed or bounded. For example, the boundary condition apparatus (block 20) may be a partial, conductive enclosure that partially surrounds the object of interest.

The one or more antennas (block 22) may be any apparatus (e.g., detectors, sensors, transmitting, receiving components, etc.) capable of delivering and sampling/collecting electromagnetic energy (e.g., microwaves) contemplated to be used in microwave tomography and in combination with processing apparatus (block 12) of the system 10. As used herein, each antenna of the one or more antennas (block 22) may include a transmitting portion, e.g., to deliver electromagnetic energy, and a receiving portion, e.g., to sample/collect electromagnetic energy, which may or may not be the same portion. During the imaging of an object, the one or more antennas (block 22) may be positioned relative to the object so as to be capable to deliver electromagnetic energy to irradiate the object resulting in scattered electromagnetic energy (also know as the resultant scattered field) and also sample the scattered electromagnetic energy resulting from the irradiation.

The one or more antennas (block 22) may include more than about 1 antenna, about 2 antennas, about 3 antennas, about 4 antennas, about 5 antennas, about 6 antennas, about 8 antennas, about 10 antennas, about 12 antennas, about 16 antennas, about 20 antennas, about 24 antennas, and about 36 antennas and/or less than about 2 antennas, about 3 antennas, about 4 antennas, about 5 antennas, about 6 antennas, about 8 antennas, about 10 antennas, about 12 antennas, about 16 antennas, about 20 antennas, about 24 antennas, and about 36 antennas. Further, the one or more antennas (block 22) may be spaced in any manner capable of delivering electromagnetic energy to irradiate the object and also sampling the resultant scattered field.

Figure 9:
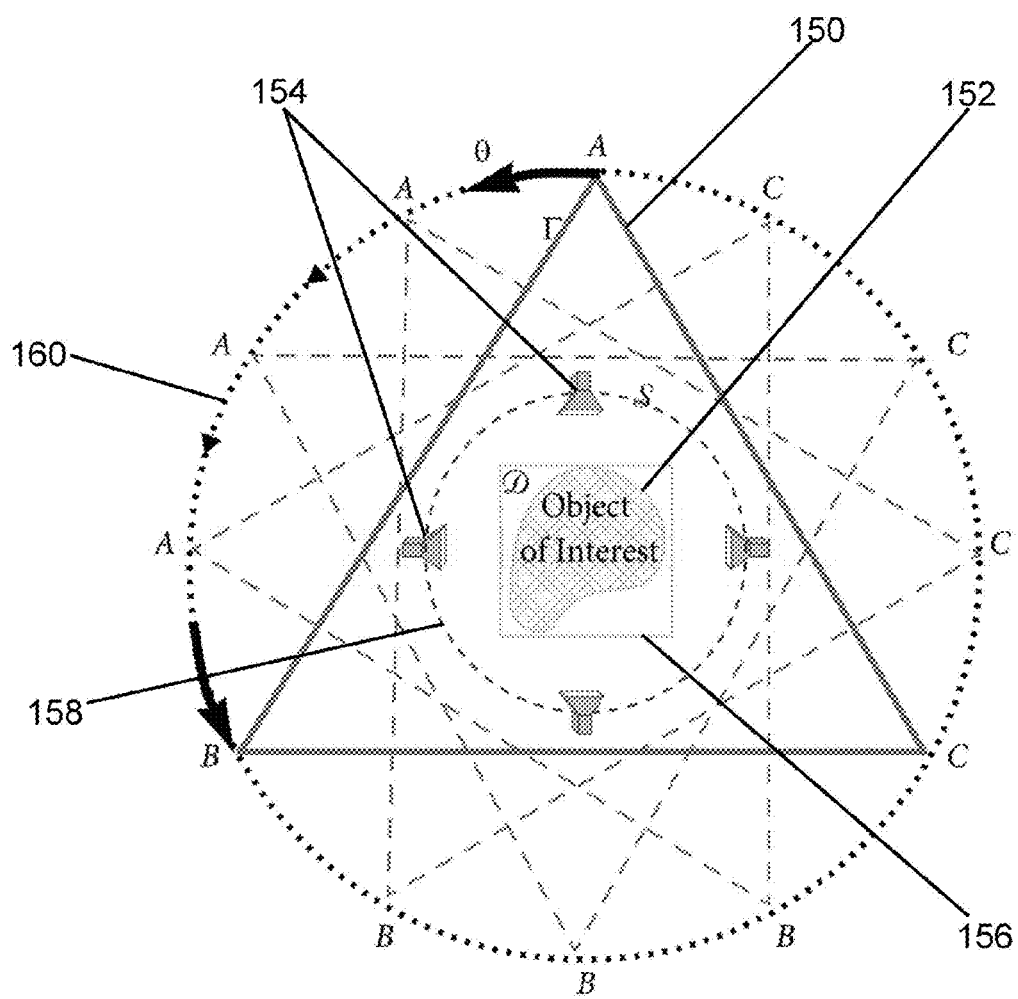
FIG. 9 depicts an exemplary boundary condition apparatus, i.e., a rotatable, triangular enclosure.

In at least one embodiment, the antennas (block 22) may be equilaterally spaced around a target area (e.g., the target area may be the area where an object to be imaged may be located). For example, in an exemplary MWT system that includes four equilaterally-spaced antennas, the first antennas may be located at 0 degrees, the second antenna may be located at 90 degrees, the third antenna may be located at 180 degrees, and the fourth antenna may be located at 270 degrees about the target area (e.g., as shown in FIG. 9). Exemplary antenna configurations are described further herein with respect to FIGS. 3-13.

The positions or locations of the boundary condition apparatus (block 20) and the one or more antennas (block 22) with respect to each other (e.g., the distance therebetween, etc.) is used in the exemplary methods and systems described herein. In at least one embodiment, the location of the boundary condition apparatus (block 20) and each of antennas (block 22) may be determined using a calibration procedure (e.g., using a laser calibration system, using the antennas themselves, etc.) before imaging an object of interest. In at least another embodiment, the boundary condition apparatus (block 20) and the antennas (block 22) may be movably or fixedly attached to a structure (e.g., a ring) such that their locations with respect to one another are known.

As described herein, generally, the boundary condition apparatus (block 20) and the one or more antennas are configured to be utilized together to provide a plurality of different incident fields (e.g., fields incident on an object of interest) to result in a plurality of different scattered fields. To provide the plurality of different incident fields, the boundary condition apparatus (block 20) is configured to present at least two, or a plurality of, different boundary conditions relative to the one or more antennas (block 22). The boundary condition apparatus (block 20) and the one or more antennas (block 22) may operate in conjunction such that the boundary condition apparatus (block 20) provides the plurality of different boundary conditions relative to the one or more antennas (block 22).

Generally, one of both of the antennas (block 22) and the boundary condition apparatus (block 20) may be configured to move relative to one another so as to provide a plurality of different boundary conditions with respect to the one or more antennas (block 22). For example, the one or more antennas (block 22) may be fixed (e.g., non-movable) relative to an object of interest, or the target area where the object is to be located, and the boundary condition apparatus (block 20) may be configured to move relative to the one or more antennas (block 22). Further, for example, the boundary condition apparatus (block 20) may be fixed relative to an object of interest, or the target area where the object is to be located, and the one or more antennas (block 22) may be configured to move relative to the boundary condition apparatus (block 20). And still further, for example, both the boundary condition apparatus (block 20) and the one or more antennas (block 22) may be both configured to move relative to one another and an object of interest so long as each movement by either of the boundary condition apparatus (block 20) and the one or more antennas (block 22) results in a different boundary condition with respect to the one or more antennas (block 22).

In at least one embodiment, the antennas (block 22) may be attached or affixed to the actual object of interest (e.g., attached to the object). For example, the antennas (block 22) may be attached to a human breast or limb.

In at least one embodiment, the boundary condition apparatus (block 20) includes a conductive enclosure that is configurable into multiple configurations, each configuration providing a different boundary condition. Such enclosure may extend 360 degrees around an object or less than 360 degrees around an object (e.g., the enclosure may use a single parabolic wall). The enclosure may further include at least one opening for receiving the object to be imaged.

In at least another embodiment, the boundary condition apparatus (block 20) may include a plurality of reconfigurable conductive walls (e.g., metal walls, metal coated walls, etc.). The reconfigurable conductive walls (e.g., one or more reconfigurable conductive walls) may be reconfigured into multiple configurations to provide multiple different boundary conditions and thereby provide multiple unique/different electromagnetic incident fields. Such reconfigurable conductive walls may extend 360 degrees around an object or less than 360 degrees around an object (e.g., the enclosure may use a single parabolic wall). In at least one embodiment, the boundary condition apparatus (block 20) may be a single wall or more than a single wall (e.g., one or more walls that may be positioned proximate to the object of interest) which may be configured to provide a plurality of boundary conditions relative to the antennas (block 22) and further, to provide, in conjunction with the antennas, unique/different electromagnetic incident fields (e.g., incident to the object to be imaged).

In at least one embodiment, the boundary condition apparatus (block 20) may be an equilateral triangular enclosure (e.g., as shown herein in FIGS. 4B & 9) to provide enclosed-triangle boundary conditions. Exemplary enclosures, however, may be any size and/or shape operable to assist in the imaging of an object of interest (e.g., triangle, square, octagon, pentagon, and/or any other multi-sided enclosure). Further, the exemplary enclosures may be modifiable with respect to the object and the antennas (block 22) (e.g., modifiable in orientation and/or volume). For example, an enclosure may be rotated around the object to present each of the plurality of different boundary conditions relative to the object to be imaged.

Further, an exemplary enclosure may be rotated incrementally about an object of interest until it ceases to provide different boundary conditions with respect to the one or more antennas (block 22). For example, when the enclosure is an equilateral-triangular enclosure, the enclosure may be rotated for 120 degrees (e.g., in 10 degree increments) with respect to the one or more antennas (block 22) before providing redundant boundary conditions (i.e., at 120 degrees, the equilateral-triangular enclosure "repeats" the enclosed-triangle boundary condition with respect to the antennas). In this example, the volume of the enclosure will not have changed but the orientation of the surfaces of the enclosure with respect to the object and the antennas (block 22) will have changed.

In other exemplary systems, the volume of the enclosure may be changed to provide different boundary conditions. For example, a surface of the enclosure may be moved towards or away from the object of interest and the one or more antennas to change the volume of the enclosure. Further, for example, an enclosure may be deformed (e.g., stretch, deflected, compressed, etc.) to change the orientation, shape, and/or volume of the enclosure.

As described herein, each different boundary condition provided by the boundary condition apparatus (block 20) may provide a different electromagnetic incident field. As a result, each different boundary condition may provide unique scattered electromagnetic energy, or scattered field, when an object of interest is irradiated with electromagnetic energy for each different boundary condition, which may be utilized in the reconstruction of an image of the object as generally described herein with reference to FIG. 2.

Figure 2:
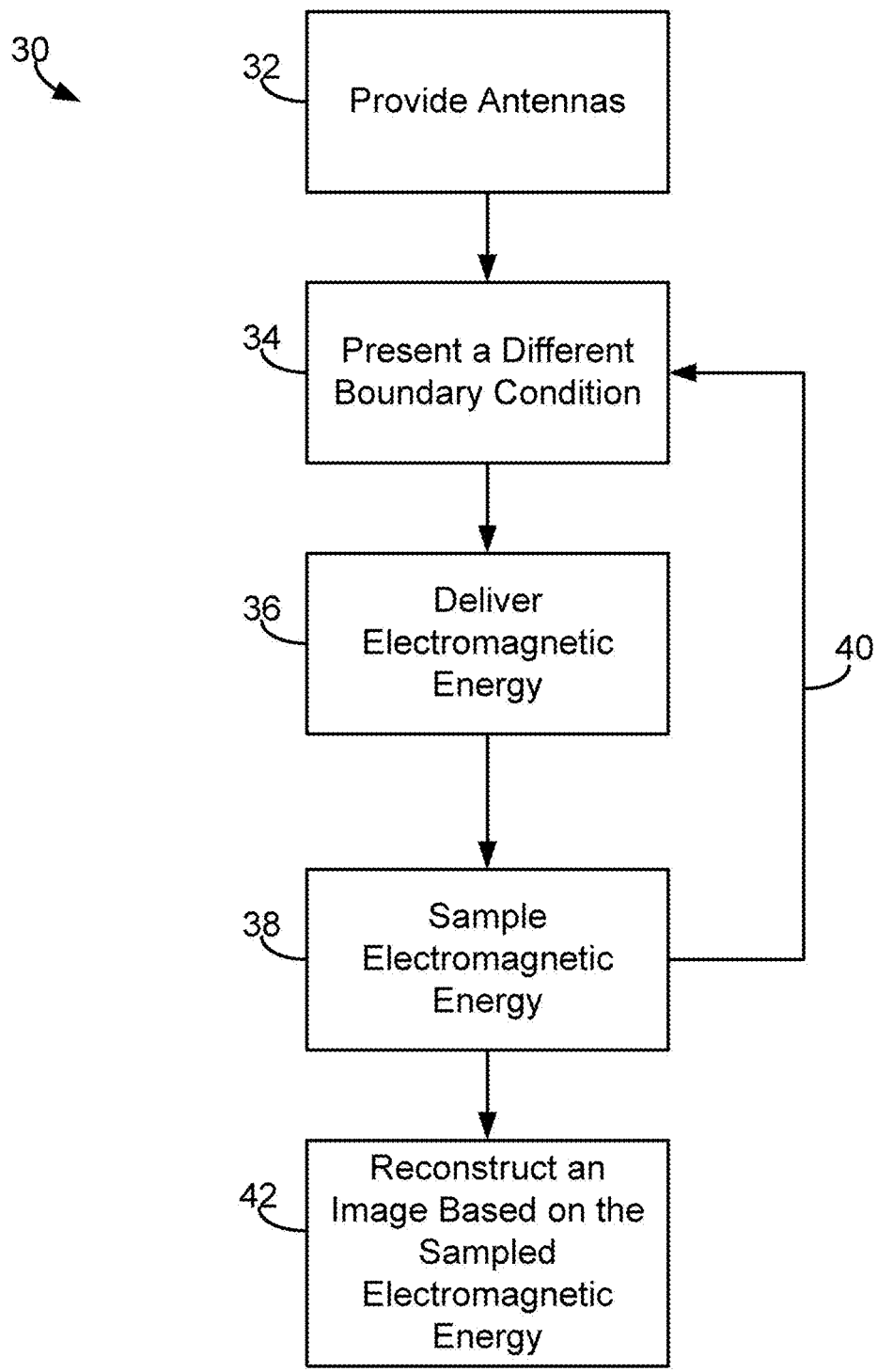
FIG. 2 is a flow chart depicting an exemplary microwave tomography imaging method.

A flow chart of an exemplary imaging method 30 for imaging an object is depicted in FIG. 2. One will recognize that one or more of the blocks of functionality described herein may be carried out using one or more programs or routines, and/or any other components of an imaging system (e.g., the imaging system 10 of FIG. 1).

Generally, the method 30 provides one or more antennas (block 32). The antennas, as well as the remainder of the system used in method 30, may be similar to the antennas (block 22), and system 10 described herein with reference to FIG. 1. The method 30 further includes presenting a different boundary condition (block 34), e.g., using the boundary condition apparatus (block 20) described herein with reference to FIG. 1. In at least one embodiment, the method 30 may use a system that includes a fixed array of antennas and an enclosure that is rotatable relative to the fixed array of antennas to present a plurality of different boundary conditions relative to the antennas.

For each different boundary condition presented (block 34), the method 30 includes delivering electromagnetic energy (e.g., electromagnetic energy generated by a microwave source at a frequency in the range of about 0.3 GHz to about 20 GHz) to irradiate the object (block 36) to present a different electromagnetic incident field upon the object (i.e., different electromagnetic incident field for each different boundary condition) and sampling the scattered electromagnetic energy (block 38).

In other words, delivering electromagnetic energy (block 36) results in scattered electromagnetic energy. While delivering electromagnetic energy (block 36), the method 30 also samples or collects the electromagnetic energy (block 38) (e.g., using one or more antennas within the enclosure) to be used in reconstruction of an image of the object.

In one or more embodiments, the electromagnetic energy may be delivered with a single antenna while the other antennas are configured to receive/collect electromagnetic energy (e.g., electromagnetic scattering data). Further, the antenna that is delivering the electromagnetic energy may also be configured to receive/collect electromagnetic energy. Also, each antenna may deliver electromagnetic energy sequentially while each of the antennas sample the electromagnetic energy (e.g., at the same time or sequentially).

In other words, electromagnetic energy may be delivered with each of the one or more antennas individually until each antenna has individually delivered electromagnetic energy to irradiate the object (e.g., for each of the plurality of different boundary conditions). For example, an exemplary imaging system may include four antennas. When one antenna of the four antennas delivers electromagnetic energy, each of the four antennas may sample electromagnetic energy resulting in four scattering measurements (e.g., 1 transmitter×4 receivers=4 scattering measurements). Further, each antenna may also transmit or deliver electromagnetic energy while all 4 antennas collect data such that 4 transmitters×4 receivers=16 scattering measurements.

As described herein, the method 30 may deliver electromagnetic energy from each antenna (block 36) and sample electromagnetic energy (block 38) for each different boundary condition, which is represented by the loop-back arrow 40 returning from sampling electromagnetic energy (block 38) to presenting a different boundary condition (block 34). In other words, scattered electromagnetic energy, or scattering data, is collected from each antenna for each different boundary condition. In at least one embodiment, at each different boundary condition, electromagnetic energy is delivered using each antenna while all the antennas (including the transmitting antenna) are configured to record electromagnetic energy.

For example, if the system includes four antennas and is configured to provide twenty-four different boundary conditions (e.g., boundary condition apparatus being an equilateral-triangular conductive enclosure configured to be rotated in 5 degree increments position, which creates 24 unique boundary conditions, through 120 degrees), electromagnetic energy may be delivered by each antenna individually and collected by each antenna for each different configured boundary resulting in at 288 scattering measurements (i.e., 4 transmitters×4 receivers×24 different boundary conditions=288 scattering measurements).

After electromagnetic energy has been delivered for each antenna and sampled at all the antennas for each of the different boundary conditions, an image representative of the object or a portion thereof may be reconstructed (e.g., using inversion) based on the sampled electromagnetic energy (block 42). Exemplary methods of reconstructing an image of an object using simulated sampled electromagnetic energy are described herein with reference to FIGS. 3-13.

Exemplary Problem Formulation

The following reconstructed 2D transverse magnetic imaging examples have been generated using simulated MWT systems and single-frequency synthetic data. Further, in the following examples, the weighted $L_2$-norm total variation multiplicative-regularized Gauss-Newton inversion (MR-GNI) was used for all inversions, and the data collected at all positions using multiple boundary condition was inverted simultaneously.

Further, the following exemplary problem formulation may be used with the exemplary imaging systems and methods described herein. The MWT problem for the 2D Transverse Magnetic case may be utilized where time-harmonic fields are used to interrogate an object of interest, or object to be imaged. Thus, a time factor of $\exp(-j\omega t)$ may be implicitly assumed. Consider a bounded imaging domain $\mathcal{D} \subset \mathbb{R}^2$ containing a non-magnetic object of interest, or object to be imaged, and a measurement domain $\mathcal{S} \subset \mathbb{R}^2$ outside of the object of interest. The object may be immersed in a known non-magnetic homogeneous matching fluid with a relative complex permittivity of $\epsilon_b$. In the following formulations, $\mathcal{D}$ and $\mathcal{S}$ are assumed to be located either within a Perfect Electric Conductor (PEC) of arbitrary shape, i.e., an enclosed-region boundary condition, or within an open region environment, i.e., an open-region boundary condition. In any case, the boundary condition of the environment is assumed to be known.

The complex electric contrast function is defined as $$\chi(q) \triangleq \frac{\epsilon_r(q) - \epsilon_b}{\epsilon_b} \qquad (1)$$

where q denotes a position vector in D and $\epsilon_r(q)$ is the unknown relative complex permittivity of the object at q.

The object of interest may be successively interrogated with a number of known incident fields $E_t^{inc}$, where $t=1, \ldots, T_x$ denotes the number of the active transmitter. Interaction of the incident field $E_t^{inc}$ with the object results in the total field $E_t$. The total and incident electric fields are then measured by some receiver antennas located on $\mathcal{S}$. Thus, the scattered electric field, $E_{meas,t}^{scat} \triangleq E_t - E_t^{inc}$ known at the receiver positions on $\mathcal{S}$. The goal is to find the electric contrast $\chi$ in a bounded imaging domain $\mathcal{D}$, which contains the object to be imaged, from the measured scattered fields $E_{meas,t}^{scat}$ on $\mathcal{S}$. The MWT problem may then be formulated as the minimization over $\chi$ of the Least-Squares (LS) data misfit cost-functional:

$$C^{LS}(\chi) = \eta_S \sum_{t=1}^{T_x} \|E_t^{scat}(\chi) - E_{meas,t}^{scat}\|_S^2 \quad (2)$$

where $E_t^{scat}(\chi)$ is the simulated scattered field at the observation points corresponding to the predicted contrast $\chi$ for the tth transmitter, and $\|\bullet\|_S$ denotes the $L_2$-norm on $S$. $S$. The simulated scattered field $E_t^{scat}(\chi)$ may be simulated using any numerical technique such as the Finite-Element, Finite-Difference, or Method of Moments techniques. Further this simulated scattered field must take into account the appropriate boundary conditions for the different configurations being modeled. (see, e.g., P. Mojabi, C. Gilmore, A. Zakaria, and J. LoVetri, "Biomedical microwave inversion in conducting cylinders of arbitrary shapes," in 13th International Symposium on Antenna Technology and Applied Electromagnetics and the Canadian Radio Science Meeting (ANTEM/URSI), February 2009, pp. 1-4). The weighting $\eta_S$ is chosen to be $$\eta_S = \left( \sum_{t=1}^{T_x} \|E_{meas,t}^{scat}\|_S^2 \right)^{-1}. \quad (3)$$

To treat the ill-posedness of the problem, the multiplicative regularized cost-functional at the nth iteration of the algorithm may be formed as follows (see, e.g., P. Mojabi and J. LoVetri, "Microwave biomedical imaging using the multiplicative regularized Gauss-Newton inversion," IEEE Antennas and Wireless Propagation Letters, vol. 8, pp. 645-648, July 2009; A. Abubakar, T. Habashy, V. Druskin, L. Knizhnerman, and D. Alumbaugh, "2.5D forward and inverse modeling for interpreting low-frequency electromagnetic measurements," Geophysics, vol. 73, no. 4, pp. F165-F177, July-August 2008; and P. Mojabi and J. LoVetri, "Overview and classification of some regularization techniques for the Gauss-Newton inversion method applied to inverse scattering problems," IEEE Trans. Antennas Propag., vol. 57, no. 9, pp. 2658-2665, September 2009):

$$C_n(\chi) = C^{LS}(\chi) C_n^{MR}(\chi). \quad (4)$$

The multiplicative regularizer $C_n^{MR}$ as the weighted $L_2$-norm total variation of the unknown contrast may be defined as follows (see, e.g., P. Mojabi and J. LoVetri, "Microwave biomedical imaging using the multiplicative regularized Gauss-Newton inversion," IEEE Antennas and Wireless Propagation Letters, vol. 8, pp. 645-648, 2009; and A. Abubakar, T. Habashy, V. Druskin, L. Knizhnerman, and D. Alumbaugh, "2.5D forward and inverse modeling for interpreting low-frequency electromagnetic measurements," Geophysics, vol. 73, no. 4, pp. F165-F177, July-August 2008;):

$$C_n^{MR}(\chi) = \int_D b_n^2(q)(|\nabla \chi(q)|^2 + \alpha_n^2) dq. \quad (5)$$

Further, the weighting $b_n(q)$ may be chosen to be $$b_n(q) \triangleq A^{-\frac{1}{2}} (|\nabla \chi_n(q)|^2 + \alpha_n^2)^{-\frac{1}{2}}. \quad (6)$$

where $\chi_n$ denotes the reconstructed contrast at the (n−1)th iteration of the algorithm, $\nabla$ denotes the spatial gradient operator with respect to the position vector q, and A is the area of $D$. The choice of the positive parameter $\alpha_n^2$ is further explained herein.

In the discrete form of the MWT problem, the contrast function $\chi(d)$ may be discretized into a complex vector $\underline{\chi}$. The measured scattered data on the discrete measurement domain $D$ is denoted by the complex vector $\underline{E}_{meas}^{scat}$. The vector $\underline{E}_{meas}^{scat}$ is the stacked version of the measured scattered fields for each transmitter. Assuming that the tth transmitter is active, the simulated scattered field corresponding to the predicted contrast at the nth iteration of the Gauss-Newton Inversion algorithm, $\underline{\chi}_n$, is denoted by $\underline{E}_{t,n}^{scat}$. The vector $\underline{E}_n^{scat}$ is then found by stacking $\underline{E}_{t,n}^{scat}$. The positive parameter $\alpha_n^2$ may be chosen to be $F^{LS}(\underline{\chi}_n)/\Delta A$ where $F^{LS}$ represents the discrete form of $C^{LS}$ and $\Delta A$ is the area of a single cell in the uniformly discretized domain $D$.

Applying the Gauss-Newton Inversion algorithm to the discrete form of (4), the contrast vector at the nth iteration of the inversion algorithm may then be updated as $\underline{\chi}_{n+1} = \underline{\chi}_n + v_n \Delta \underline{\chi}_n$ where $v_n$ is an appropriate step length and $\Delta \underline{\chi}_n$ is the correction vector. For example, a line search algorithm may be utilized for this work (see, e.g., A. Abubakar, T. Habashy, V. Druskin, L. Knizhnerman, and D. Alumbaugh, "2.5D forward and inverse modeling for interpreting low-frequency electromagnetic measurements," Geophysics, vol. 73, no. 4, pp. F165-F177, July-August 2008; and T. M. Habashy and A. Abubakar, "A general framework for constraint minimization for the inversion of electromagnetic measurements," Progress in Electromagnetics Research, vol. 46, pp. 265-312, 2004). The correction vector can be found from $$(\underline{J}_n^H \underline{J}_n - \beta_n \underline{L}_n) \Delta \underline{\chi}_n = \underline{J}_n^H \underline{d}_n + \beta_n \underline{L}_n \underline{\chi}_n \quad (7)$$

whereas $\underline{L}_n$ represents the discrete form of the $\nabla \cdot (b_n^2 \nabla)$ operator, $\underline{J}_n$ is the Jacobian matrix which contains the derivatives of the simulated scattered field with respect to the contrast and evaluated at $\underline{\chi} = \underline{\chi}_n$. The discrepancy vector $\underline{d}_n$ is given as $\underline{d}_n = \underline{E}_{meas}^{scat} - \underline{E}_n^{scat}$ and $\beta_n = \|\underline{d}_n\|^2$ (see, e.g., P. Mojabi and J. LoVetri, "Microwave biomedical imaging using the multiplicative regularized Gauss-Newton inversion," IEEE Antennas and Wireless Propagation Letters, vol. 8, pp. 645-648, 2009; A. Abubakar, T. Habashy, V. Druskin, L. Knizhnerman, and D. Alumbaugh, "2.5D forward and inverse modeling for interpreting low frequency electromagnetic measurements," Geophysics, vol. 73, no. 4, pp. F165-F177, July-August 2008; and P. Mojabi, "Investigation and development of algorithms and techniques for microwave tomography," Ph.D. dissertation, University of Manitoba, Winnipeg, Manitoba, Canada, 2010, URL: http://mspace.lib.umanitoba.ca/handle/1993/3946).

The regularization operator $\underline{L}_n$ is a weighted Laplacian operator, which provides an edge-preserving regularization (see, e.g., P. Charbonnier, L. Blanc-Féraud, G. Aubert, and M. Barlaud, "Deterministic edge-preserving regularization in computed imaging," IEEE Trans. Image Processing, vol. 6, no. 2, pp. 298-311, February 1997). The exemplary methods and systems described herein utilize the Gauss-Newton algorithm, sometimes referred to as the Multiplicative Regularized Gauss-Newton Inversion (MR-GNI) algorithm, to invert the synthetic data sets. All synthetic data sets are generated on a different grid than the ones used in the inversion algorithm. Further, 3% RMS additive white noise was added to the synthetic data set using the formula to simulate real-world conditions (see, e.g., A. Abubakar, P. M. van den Berg, and S.

Y. Semenov, "A robust iterative method for Born inversion," IEEE Trans. Geosci. Remote Sensing, vol. 42, no. 2, pp. 342-354, February 2004):

$$E_{meas,t}^{scat} = E_t^{scat,fwd} + \max[\forall_t\, E_t^{scat,fwd}]\frac{\eta}{\sqrt{2}}(\vartheta_1 + j\vartheta_2) \quad (8)$$

where $\underline{E}_t^{scat,fwd}$ is the scattered field on the measurement domain due to the tth transmitter obtained by the forward solver, $\underline{\vartheta}_1$ and $\underline{\vartheta}_2$ are two real vectors whose elements are uniformly distributed zero-mean random numbers between −1 and 1, and η=0.03. The vector $\underline{E}_{meas}^{scat}$, constructed by stacking the vectors $\underline{E}_{meas,t}^{scat}$, may then used to test inversion algorithms against synthetic data sets.

Simultaneous Inversion of Scattering Data for Two Different Boundary Conditions

As described previously, many MWT algorithms used to invert data from MWT systems assume that the matching fluid extends to infinity, not to the boundary of the dielectric casing. That is, such algorithms assume that the scattering data is collected in a homogeneous embedding. In other words, the boundary condition for these problems is the Sommerfeld radiation condition. The scattering data collected in such systems, i.e., systems having an open-region boundary condition, will be referred herein as open-region scattering data.

The use of a conductive enclosure in a MWT imaging system imposes a zero boundary condition, i.e., an enclosed-region boundary condition, on the total field, which can be modeled within the utilized inversion algorithm. The scattering data collected in such enclosed-region boundary condition systems will be referred to as enclosed-region scattering data.

Calculation of the Jacobian matrix and the simulated scattered field may utilize repeated forward solver calls. For the open-region boundary condition, the method of moments (MoM) with the conjugate gradient algorithm accelerated by the fast Fourier transform (CG-FFT) may be used. The CG-FFT forward solver may also be accelerated by employing the marching-on-in-source-position technique (see, e.g., A. G. Tijhuis, K. Belkebir, and A. C. S. Litman, "Theoretical and computational aspects of 2-D inverse profiling," IEEE Trans. Geosci. Remote Sensing, vol. 39, no. 6, pp. 1316-1330, 2001).

A finite element method (FEM) based on triangular elements for the enclosed-region boundary conditions may be used to model arbitrary boundaries with both straight and curved edges. As the FEM mesh is based on triangles, and the inverse solver is based on rectangular pulse-basis functions, interpolation between the two meshes with a bi-linear interpolation algorithm may be used (see, e.g., P. Mojabi, C. Gilmore, A. Zakaria, and J. LoVetri, "Biomedical microwave inversion in conducting cylinders of arbitrary shapes," in 13th International Symposium on Antenna Technology and Applied Electromagnetics and the Canadian Radio Science Meeting (ANTEM/URSI), February 2009, pp. 1-4).

Figure 3:
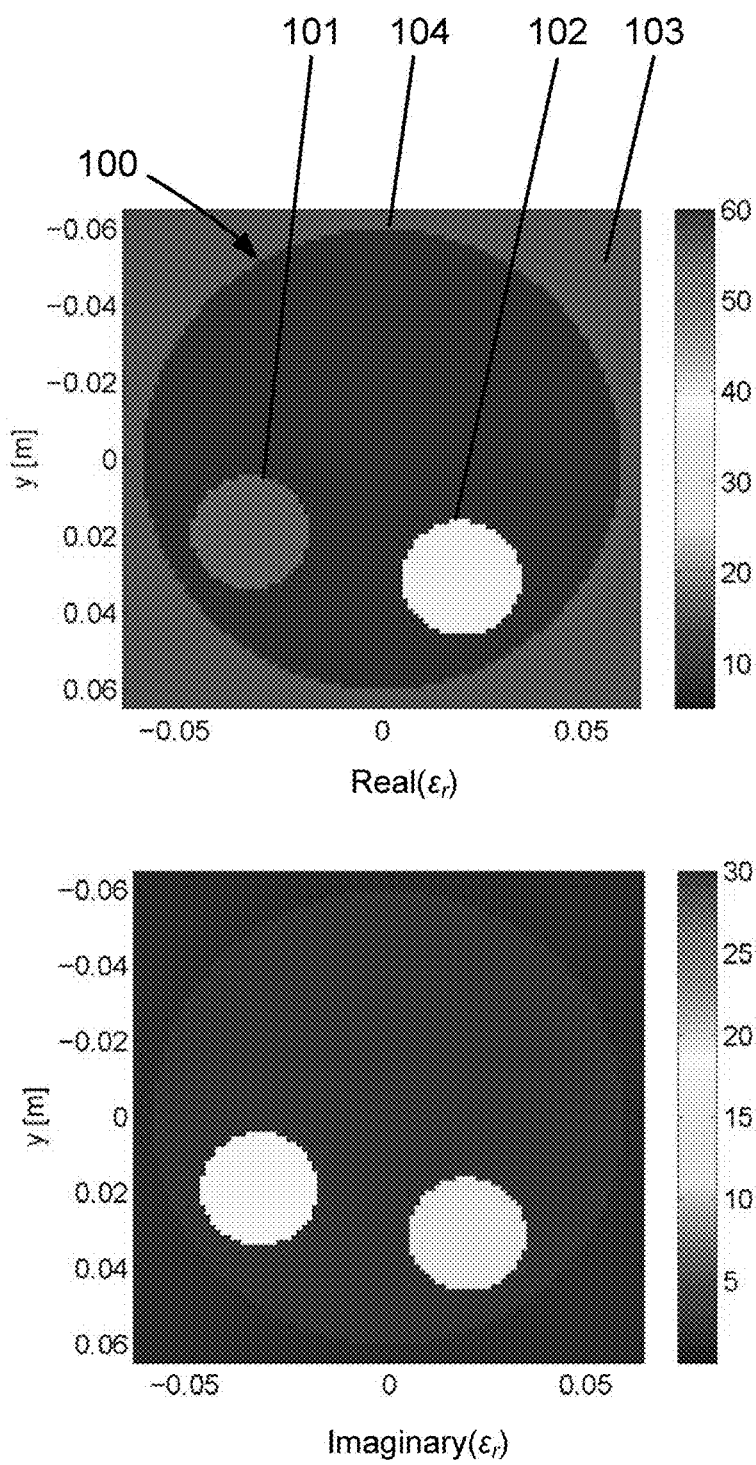
FIG. 3 depicts an exemplary simulated object of interest, e.g., to be imaged by the systems and/or methods described herein.

The first exemplary simulated object 100 to be imaged includes three circular regions 101, 102, 103 as shown in FIG. 3. The simulated object 100 of FIG. 3, as well as the reconstructed images of the object 100 shown in FIGS. 5-8 & 10, are depicted for both the real and imaginary parts of the object's relative complex permittivity.

The first two circular regions 101, 102 of the object of interest 100 have the same radius of 0.015 meters (m) and their relative complex permittivities are $\in_{r,tum}$=56.4+j18.05 and $\in_{r,fibro}$=36.47+j11.73, respectively, at the frequency of 1 GHz. These two circular regions 101, 102 are surrounded by another circular region 104 with radius of 0.06 m, which has a relative permittivity of $\in_{r,adip}$=7.85+j1.9. The relative complex permittivities $\in_{r,tum}$, $\in_{r,fibro}$, and $\in_{r,adip}$ represent the relative complex permittivity of human breast tumor, fibroglandular, and adipose tissue, respectively, based on the single-pole Debye model (see, e.g., M. Lazebnik, M. Okoniewski, J. Booske, and S. Hagness, "Highly accurate debye models for normal and malignant breast tissue dielectric properties at microwave frequencies," IEEE Microwave and Wireless Components Letters, vol. 17, no. 12, pp. 822-824, December 2007). The exemplary simulated object of interest 100 is immersed in a background medium 103 of relative complex permittivity of 15+j.

Figure 4A:
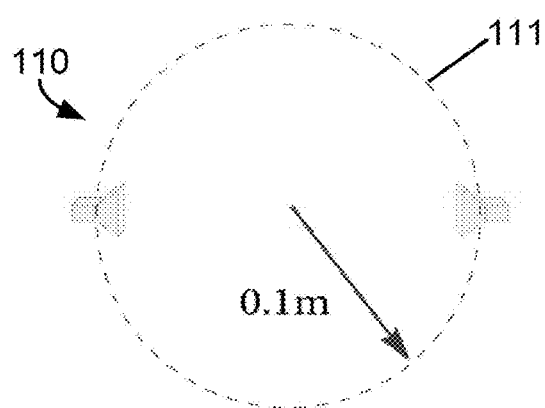
FIGS. 4A-C depict an open-region boundary condition, an enclosed-triangle boundary condition, and an enclosed-square boundary condition, respectively.
Figure 4B:
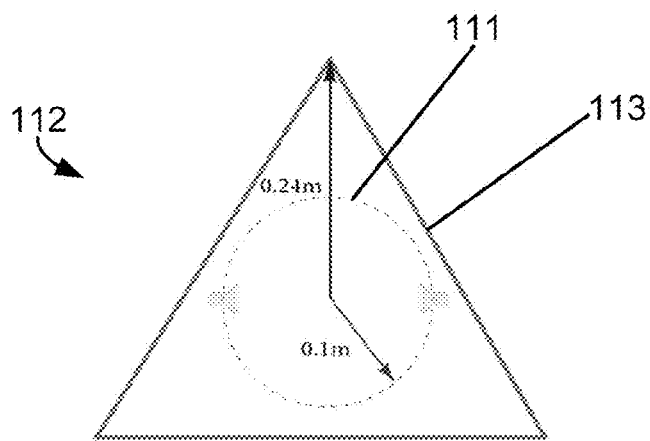
Figure 4C:
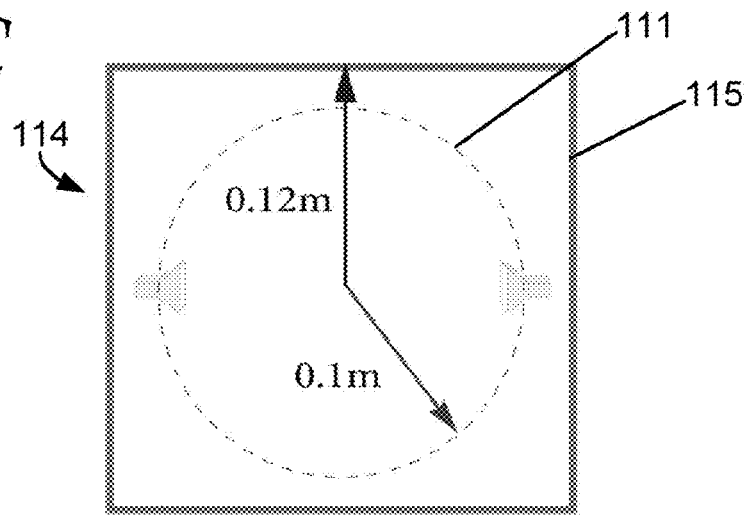

In the following examples, three boundary conditions are used for the simulated collection of scattered electromagnetic energy, or scattering data: an open-region boundary condition as shown in FIG. 4A; an enclosed-equilateral-triangle boundary condition as shown in FIG. 4B, and an enclosed-square boundary condition as shown in FIG. 4C. In each boundary condition, the transmitters and receivers are evenly spaced on a circle 111 of radius 0.1 m and the frequency of operation is 1 GHz.

Further, two different antenna configurations are used to simulate the collection of the scattered electromagnetic energy, or scattering data. In the first antenna configuration, 7 antennas (i.e., 7 transmitters and 7 receivers) are used for delivering electromagnetic energy and sampling the scattered electromagnetic energy on the measurement circle 111, and in the second antenna configuration, 16 antennas (i.e., 16 transmitters and 16 receivers) are used for delivering electromagnetic energy and sampling the scattered electromagnetic energy on the measurement circle 111.

Figure 5A:
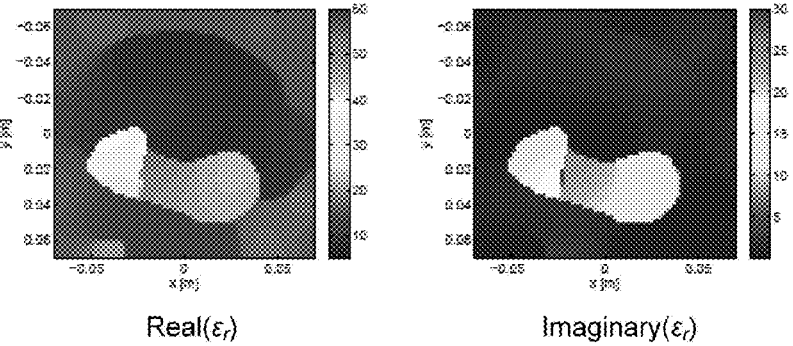
FIG. 5A provides exemplary images of the object of interest of FIG. 3 reconstructed using scattered electromagnetic energy collected in a simulated MWT system using seven antennas and the open-region boundary condition of FIG. 4A.
Figure 5B:
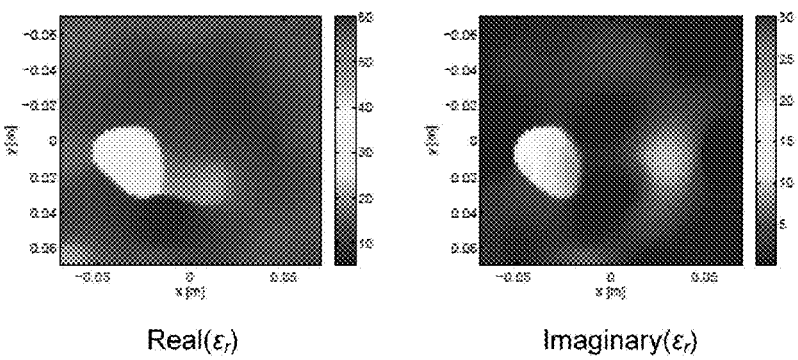
FIG. 5B provides exemplary images of the object of interest of FIG. 3 reconstructed using scattered electromagnetic energy collected in a simulated MWT system using seven antennas and the enclosed-triangle boundary condition of FIG. 4B.
Figure 5C:
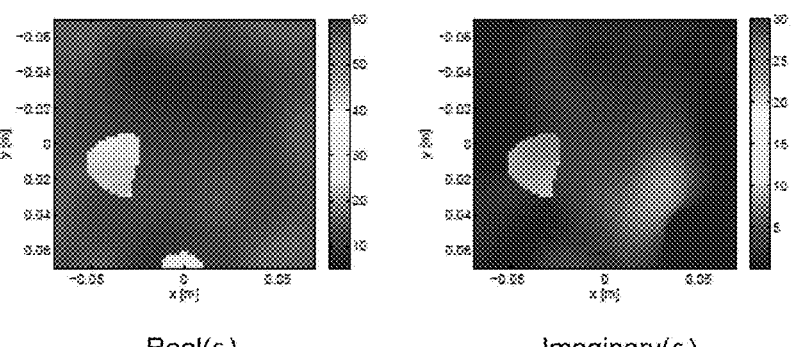
FIG. 5C provides exemplary images of the object of interest of FIG. 3 reconstructed using scattered electromagnetic energy collected in a simulated MWT system using seven antennas and the enclosed-enclosed boundary condition of FIG. 4C.

Exemplary images of the object of interest 100 reconstructed using the first antenna configuration and each of the open-region boundary condition 110, the enclosed-equilateral-triangle boundary condition 112, and the enclosed-square boundary condition 114 are provided herein in FIGS. 5A-5C. More specifically, an image of the object of interest 100 reconstructed using inversion of scattering data obtained using the first antenna configuration with the open-region boundary condition 110 is shown in FIG. 5A, an image of the object of interest 100 reconstructed using inversion of scattering data obtained using the first antenna configuration with the enclosed-equilateral-triangle boundary condition 112 is shown in FIG. 5B, and an image of the object of interest 100 reconstructed using inversion of scattering data obtained using the first antenna configuration with the enclosed-square boundary condition 114 is shown in FIG. 5C.

To reconstruct images based on scattering data obtained using two different boundary conditions, the exemplary systems and methods described herein may utilize an inversion algorithm to simultaneously invert the scattering data obtained in both boundary conditions. For example, for the open-region boundary condition 110 (e.g., in the following formulations, the open-region boundary condition variables are noted with "open") and one of the enclosed boundary conditions 112, 114 (e.g., in the following formulations, the enclosed-region boundary condition variables are noted with "PEC," which, as noted herein, represents Perfect Electric Conductor), the following regularized cost-functional may be utilized:

$$C_n(\chi) = \frac{1}{2}[C_{open}^{LS}(\chi) + C_{pec}^{LS}(\chi)]C_n^{MR}(\chi). \qquad (9)$$

The cost-functionals $C_{open}^{LS}$ and $C_{pec}^{LS}$ represent the data misfit cost-functional (e.g., see (2) above), for the open-region boundary condition 110 and enclosed boundary conditions 112, 114, respectively. Different boundary conditions manifest themselves in a different modeled scattered field $E_t^{scat}(\chi)$ within each cost functional. The regularizer $C_n^{MR}$ (provided herein in (5)) and the steering parameter $\alpha_n^2$, in the discrete domain, may be given as the following:

$$\alpha_n^2 = \frac{1}{2}\frac{\mathcal{F}_{open}^{LS}(\chi_n) + \mathcal{F}_{pec}^{LS}(\chi_n)}{\Delta A}. \qquad (10)$$

where $F_{open}^{LS}(\chi_n)$ and are the discrete forms of $C_{open}^{LS}(\chi_n)$. The correction $\Delta \chi_n$ may then be found by solving the following:

$$(\underline{A}_n^H \underline{A}_n - \beta_n \mathcal{L}_n)\Delta\chi_n = \underline{A}_n^H \underline{d}_n^{open,pec} + \beta_n \mathcal{L}_n \chi_n. \qquad (11)$$

The complete matrix $\underline{A}_n$ may be constructed as $$A_n = \begin{pmatrix} \sqrt{\eta_{S,open}} \underline{J}_{open,n} \\ \sqrt{\eta_{S,pec}} \underline{J}_{pec,n} \end{pmatrix} \qquad (12)$$

where $\underline{J}_{open,n}$ and $\underline{J}_{pec,n}$ are the Jacobian matrices for the open-region boundary condition and enclosed boundary conditions at the nth iteration of the inversion algorithm respectively. The normalization factors for the open-region boundary condition and enclosed-region boundary condition scattering data, $\eta S_{,open} \eta S_{,pec}$, respectively are also given by (3).

The vector $\underline{d}_n^{open,pec}$ is given as $$d_n^{open,pec} = \begin{pmatrix} \underline{d}_{open,n} \\ \underline{d}_{pec,n} \end{pmatrix} = \begin{pmatrix} E_{open,n}^{scat} - E_{meas,open}^{scat} \\ E_{pec,n}^{scat} - E_{meas,pec}^{scat} \end{pmatrix} \qquad (13)$$

where $\underline{E}_{open,n}^{scat}$ and $\underline{E}_{pec,n}^{scat}$ are the complex vectors containing the simulated scattered field at the observation points corresponding to the predicted contrast $\chi_n$ for the open-region boundary condition and enclosed-region boundary conditions, respectively. The complex vectors $\underline{E}_{meas,open}^{scat}$ and $\underline{E}_{meas,pec}^{scat}$ represent the measured data for the open-region boundary condition and enclosed-region boundary conditions, respectively. The discrete regularization operator $\mathcal{L}_n$ has already been described above and the weight of this regularization, i.e., $\beta_n$, is as follows:

$$\beta_n = F_{open}^{LS}(\chi_n) + F_{pec}^{LS}(\chi_n). \qquad (14)$$

Figure 6A:
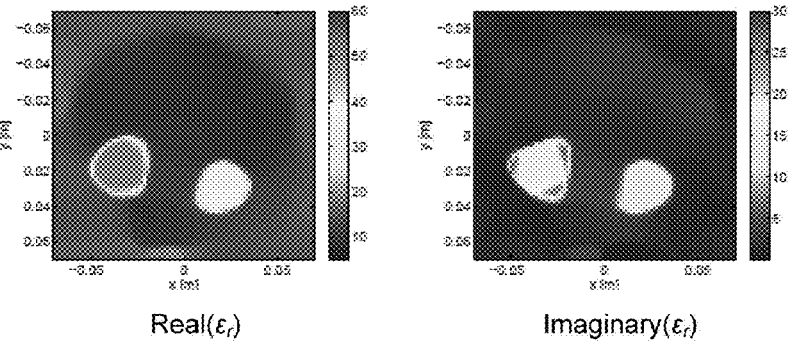
FIG. 6A provides exemplary images of the object of interest of FIG. 3 reconstructed using scattered electromagnetic energy collected in a simulated MWT system using seven antennas and the boundary conditions of FIG. 4A & FIG. 4B.
Figure 6B:
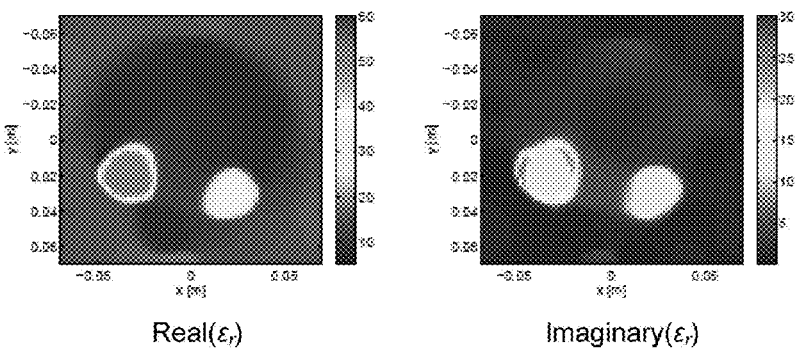
FIG. 6B provides exemplary images of the object of interest of FIG. 3 reconstructed using scattered electromagnetic energy collected in a simulated MWT system using seven antennas and the boundary conditions of FIG. 4A & FIG. 4C.
Figure 6C:
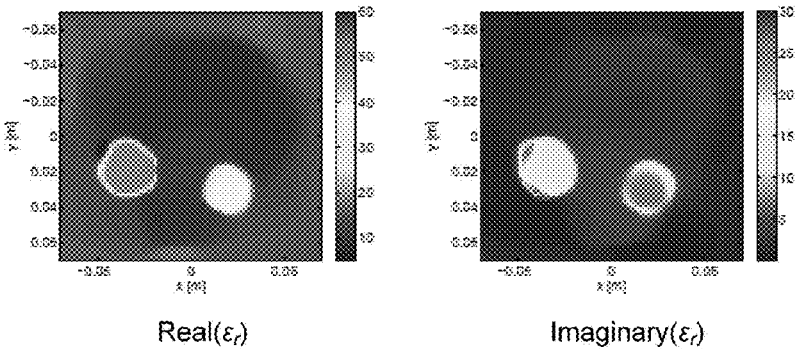
FIG. 6C provides exemplary images of the object of interest of FIG. 3 reconstructed using scattered electromagnetic energy collected in a simulated MWT system using seven antennas and the boundary conditions of FIG. 4B & FIG. 4C.

Using this inversion algorithm, the three data sets described above (e.g., obtained using the first antenna configuration, using 7 antennas, and the open-region boundary condition, the enclosed-equilateral-triangle boundary configuration, and the enclosed-square boundary configuration have been simultaneously inverted in three separate combinations to reconstruct an image of the object 100 of FIG. 3. More specifically, an image of the object of interest 100 reconstructed using the simultaneous inversion of scattering data obtained using the first antenna configuration with each of the open-region boundary condition 110 and the enclosed-equilateral-triangle boundary condition 112 is shown in FIG. 6A, an image of the object of interest 100 reconstructed using the simultaneous inversion of scattering data obtained using the first antenna configuration with each of the open-region boundary condition 110 and the enclosed-square boundary condition 114 is shown in FIG. 6B, and an image of the object of interest 100 reconstructed using the simultaneous inversion of scattering data obtained using the first antenna configuration with each of the enclosed-equilateral-triangle boundary condition 112 and the enclosed-square boundary condition 114 is shown in FIG. 6C.

When comparing FIGS. 6A-6C to FIG. 3, it can be seen that the simultaneous inversion of scattering data obtained using two different boundary conditions may be close to the true profile of the object of interest. Further, when comparing FIGS. 5A-5C to FIGS. 6A-6C, it can be also seen that the simultaneous inversion of scattering data obtained using two different boundary conditions may result in a more accurate reconstruction than inversion of scattering data obtained using a single boundary condition.

Figure 7A:
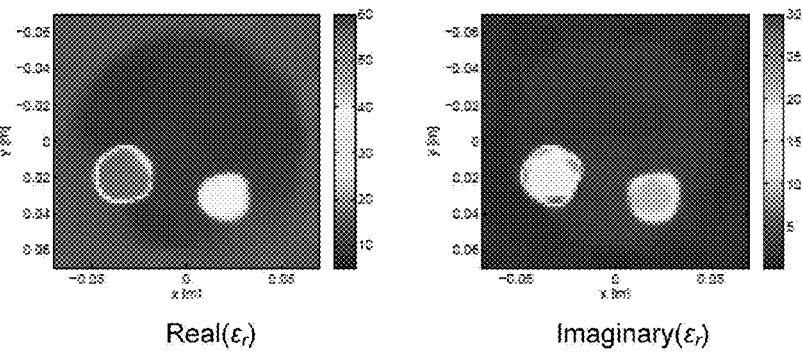
FIG. 7A provides exemplary images of the object of interest of FIG. 3 reconstructed using scattered electromagnetic energy collected in a simulated MWT system using sixteen antennas and the open-region boundary condition of FIG. 4A.
Figure 7B:
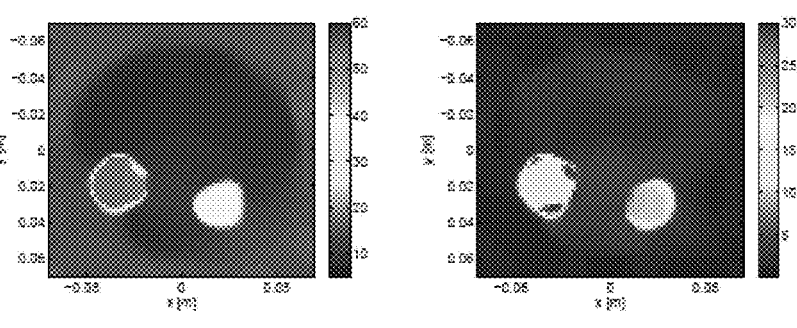
FIG. 7B provides exemplary images of the object of interest of FIG. 3 reconstructed using scattered electromagnetic energy collected in a simulated MWT system using sixteen antennas and the enclosed-triangle boundary condition of FIG. 4B.
Figure 7C:
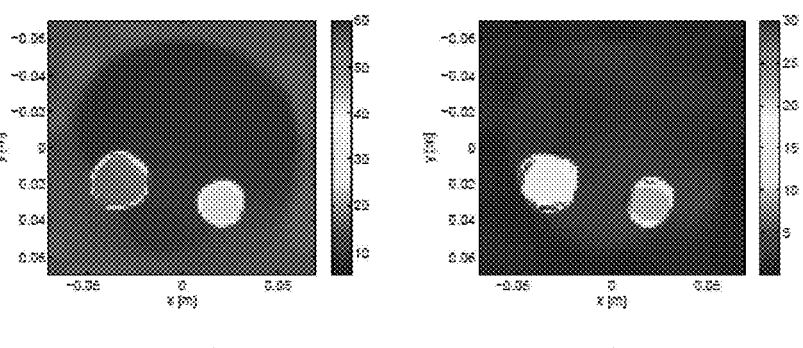
FIG. 7C provides exemplary images of the object of interest of FIG. 3 reconstructed using scattered electromagnetic energy collected in a simulated MWT system using sixteen antennas and the enclosed-square boundary condition of FIG. 4C.

As described herein, the second antenna configuration for collecting the scattering data utilized 16 antennas (e.g., thereby creating 256 scattering measurements, 16 receivers× 16 transmitters=256 scattering measurements). Exemplary reconstructed images of the object of interest reconstructed using the second antenna configuration and each of the open-region boundary condition 110, the enclosed-equilateral-triangle boundary condition 112, and the enclosed-square boundary condition 114 are provided herein in FIGS. 7A-7C. More specifically, an image of the object of interest 100 reconstructed using inversion of scattering data obtained using the second antenna configuration with the open-region boundary condition 110 is shown in FIG. 7A, an image of the object of interest 100 reconstructed using inversion of scattering data obtained using the second antenna configuration with the enclosed-equilateral-triangle boundary condition 112 is shown in FIG. 7B, and an image of the object of interest 100 reconstructed using inversion of scattering data obtained using the second antenna configuration with the enclosed-square boundary condition 114 is shown in FIG. 7C.

Further, using the inversion algorithm disclosed herein, the three data sets described above using the second antenna configuration (i.e., using 16 antennas) have been simultaneously inverted in three separate combinations to reconstruct an image of the object 100 of FIG. 3 in FIGS. 8A-C. More specifically, an image of the object of interest 100 reconstructed using the simultaneous inversion of scattering data obtained using the second antenna configuration with each of the open-region boundary condition 110 and the enclosed-equilateral-triangle boundary condition 112 is shown in FIG. 8A, an image of the object of interest 100 reconstructed using the second antenna configuration with each of the open-region boundary condition 110 and the enclosed-square boundary condition 114 is shown in FIG. 8B, and an image of the object of interest 100 reconstructed using the second antenna configuration with each of the enclosed-equilateral-triangle boundary condition 112 and the enclosed-square boundary condition 114 is shown in FIG. 8C.

In one or more embodiments, the use of a lossless or low-loss background medium or a low-loss fluid may be useful to not suppress the reflection from enclosures (e.g., enclosures providing the enclosed boundary conditions 112, 114). As used herein, a low-loss fluid may be defined as a fluid having the imaginary part of the relative complex permittivity close to zero or less than about j1. From a functional point of view, a low-loss matching medium may be defined as one with a sufficiently low loss such that sufficient scattered energy which reaches the enclosure of an enclosed boundary condition returns to the receiving antennas to produce a different measurement than would occur in the case of an open boundary condition, e.g., one having no enclosure. Further, the real part of the permittivity of the low-loss fluid may be any value so as to reduce the reflections between the matching medium and the object of interest.

For example, if a lossy background medium with the relative complex permittivity of 23.4+j20.3 at 1 GHz (see, e.g., the lossy back ground used in the system described in T. Rubaek, P. M. Meaney, P. Meincke, and K. D. Paulsen, "Non-linear microwave imaging for breast-cancer screening using Gauss-Newton's method and the CGLS inversion algorithm," IEEE Trans. Antennas Propag., vol. 55, no. 8, pp. 2320-2331, August 2007) is utilized, the reflection from an enclosure may be suppressed, and thus, simultaneous inversion of open-region boundary condition and enclosed-region boundary condition scattering data may not provide data useful for reconstruction of an object. In addition, if an object to be imaged has high loss, itself may also suppress the reflection from the enclosed boundary conditions, and thus, reduce the amount of non-redundant information.

A Rotatable Conductive Enclosure to Provide a Plurality of Different Boundary Conditions Another exemplary embodiment of boundary condition apparatus that may be configured to present a plurality of different boundary conditions may be a rotatable conductive enclosure.

For example, as shown in FIG. 9, a rotatable conductive enclosure may be a rotatable equilateral triangular metallic enclosure Γ 150, which encloses an object of interest 152 and a few antenna 154 (e.g., transceivers and receivers). The object of interest 152 may be located in the bounded imaging domain $D \subset \mathbb{R}^2$ 156, and the antennas 154 may be located on the measurement domain $S \subset \mathbb{R}^2$ 158, which is located outside of the object 152.

For the following mathematical formulation, the metallic enclosure Γ 150 is a PEC and is filled with, a lossless or low-loss matching fluid with a known relative complex permittivity of $\in_b$. To change the boundary condition of the conductive enclosure Γ 150 relative to the antennas 156 (e.g., to provide unique scattering data), the enclosure Γ 150 is rotated at angles $\theta_l \in [0°, 120°]$, l=1, ..., L, with respect to the fixed D and fixed S as depicted in FIG. 9. At the lth configuration of the enclosure Γ 150, the object 152 has been illuminated by some incident electric field, $E_{l,t}^{inc}$ where t denotes the transmitter index (t=1, ..., $T_x$).

Interaction of the incident field with the object 152 results in the total field $E_{l,t}$. The resulting field depends not only on the antenna 154 locations, but also on the orientation of the enclosure Γ 150. The total and incident electric fields may then be measured by the receiver antennas located on S 158. Thus, the scattered field at the observation points, contaminated by measurement noise, is known and may be denoted by $E_{meas,l,t}^{scat}$.

The inversion problem for this system may then be formulated as the minimization over $\chi$ of the following nonlinear least-squares data misfit cost-functional $$C^{ROT}(\chi) = \frac{1}{L}\sum_{l=1}^{L} C_l^{LS}(\chi) \qquad (15)$$

$$= \frac{1}{L}\sum_{l=1}^{L} \eta_{S,l} \sum_{t=1}^{T_x} \|E_{l,t}^{scat}(\chi) - E_{meas,l,t}^{scat}\|_S^2$$

where $E_{l,t}^{scat}(\chi)$ is the simulated scattered field on S 158 due to a predicted contrast $\chi$ when the tth transmitter is active at the lth configuration of the triangular enclosure. The normalization factor $\eta_{S,l}$ may be provided in (3) where $E_{meas,t}^{scat}$ is to be replaced with $E_{meas,l,t}^{scat}$.

Formulation (15) may be regularized by the weighted $L_2$-norm total variation multiplicative regularizer given in formulation (5). Thus, at the nth iteration of the inversion algorithm, the regularized cost-functional may be minimized as follows:

$$C_n(\chi) = C^{ROT}(\chi) C_n^{MR}(\chi). \qquad (16)$$

The positive parameter $\alpha_n^2$ in formulation (5) is chosen to be $\underline{F}^{ROT}(\chi_n)/\Delta A$ where $F^{ROT}(\chi_n)$ is the discrete form of $C^{ROT}(\chi_n)$. The correction vector $\Delta \chi_n$ may be found by solving the following:

$$\left[\left(\sum_{l=1}^{L} \eta_{S,l} \underline{J}_{l,n}^H \underline{J}_{l,n}\right) - \beta_n \underline{\mathcal{L}}_n\right] \Delta \underline{\chi}_n = \left(\sum_{l=1}^{L} \eta_{S,l} \underline{J}_{l,n}^H \underline{d}_{l,n}\right) + \beta_n \underline{\mathcal{L}}_n \underline{\chi}_n \qquad (17)$$

The matrix $\underline{J}_{l,n}$ is the Jacobian matrix corresponding to the lth rotation of the enclosure and at the nth iteration of the inversion algorithm, which may be calculated using an FEM forward solver. The weight $\beta_n$ is equal to $L \times F^{ROT}(\chi_n)$. The discrepancy vector $\underline{d}_{l,n}$ is the following:

$$\underline{d}_{l,n} = \underline{E}_{meas,l}^{scat} - \underline{E}_{l,n}^{scat}. \qquad (18)$$

Inversion results, i.e., reconstructed images, for two synthetic objects have been created with a frequency-domain FEM forward solver. For each synthetic data set, the enclosure Γ 150 shown in FIG. 9 was used, where the radius of the circumscribing circle 160 of the enclosure Γ 150 being 0.24 m. The radius of the measurement circle of domain S 158 is chosen to be 0.1 m for both synthetic data sets.

The first synthetic object is the object 100 depicted in FIG. 3. The frequency of operation is 1 GHz and 4 antenna (i.e., 4 transmitters×4 receivers=16 sets of scattering data per different boundary condition, or rotation of the enclosure Γ 150) evenly spaced about S 158 are utilized. Therefore, for the lth rotation of the enclosure Γ 150, $E_{meas,l}^{scat} \in \mathbb{C}^{16}$. Further, the enclosure Γ 150 is rotated 12 times (L=12) with a step of 15° providing 192 scattering measurements (e.g., 12 rotations×4 transmitters×4 receivers=192 scattering measurements).

An image of the object of interest 100 reconstructed using the simultaneous inversion of these 192 scattering measurements is shown in FIG. 10. As shown, the reconstruction using the rotatable enclosure Γ 150 and 4 antennas is similar to the reconstruction using the open-region boundary condition configurations with 16 antennas (shown in FIG. 7) for the object 100, and both provide a reasonable reconstruction for both the real and imaginary parts of the object's relative complex permittivity.

The second synthetic object to be analyzed is an object of interest 200 provided in FIG. 11 (e.g., this object has the same geometry as the object described in S. Semenov, R. Svenson, A. Bulyshev, A. Souvorov, A. Nazarov, Y. Sizov, V. Posukh, A. Pavlovsky, P. Repin, and G. Tatsis, "Spatial resolution of microwave tomography for detection of myocardial ischemia and infarction-experimental study on two-dimensional models," IEEE Trans. Microwave Theory Tech., vol. 48, no. 4, pp. 538-544, April 2000; and C. Gilmore, P. Mojabi, A. Zakaria, S. Pistorius, and J. LoVetri, "On super-resolution with an experimental microwave tomography system," IEEE Antennas and Wireless Propagation Letters, vol. 9, pp. 393-396, 2010)). The object 200 has different distances between its details ranging from 8 millimeters (mm) to 20 mm. The relative complex permittivity of the object 200 is 28+j2 and the background medium 202 is 25+j at the frequency of operation, which is be 2 GHz.

To collect scattered field data, 6 antennas are used (i.e., 6 transmitters and 6 receivers), and thus, $\underline{E}_{meas,l}^{scat} \in \mathbb{C}^{36}$. The enclosure Γ 150 is then rotated 48 times with a step of 2.5° to provide 1728 scattering measurements (e.g., 48 rotations×6 transmitters×6 receivers=1728 scattering measurements).

Figure 12A:
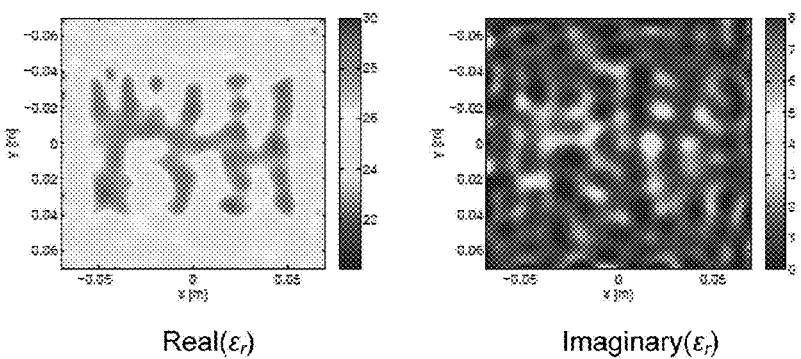
FIG. 12A provides exemplary images of the object of interest of FIG. 11 reconstructed using scattered electromagnetic energy collected in a simulated MWT system using six antennas and the rotatable, triangular enclosure of FIG. 9.
Figure 12B:
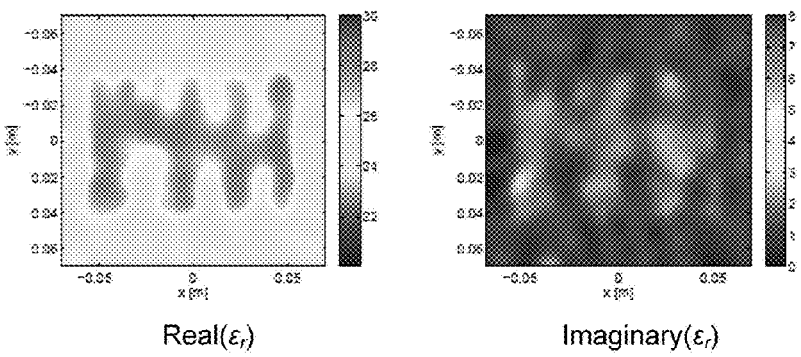
FIG. 12B provides exemplary images of the object of interest of FIG. 11 reconstructed using scattered electromagnetic energy collected in a simulated MWT system using 16 antennas and the open-region boundary condition of FIG. 4A.

An image of the object of interest 200 reconstructed using the simultaneous inversion of these 1728 scattering measurements obtained using the rotatable enclosure Γ 150 is shown in FIG. 12A. For comparison, an image of the object of interest 200 reconstructed using scattering data obtained with 16 antenna (i.e., 16 transmitters and 16 receivers) using the open-region boundary condition 110 of FIG. 4A is shown in FIG. 12B.

To obtain a further reconstructed image of the object 200, additional image enhancement methods (see, e.g., P. Mojabi and J. LoVetri, "Enhancement of the Krylov subspace regularization for microwave biomedical imaging," IEEE Trans. Med. Imag., vol. 28, no. 12, pp. 2015-2019, December 2009) may be used to obtain the final reconstructed images of both inversions. For example, enhanced reconstructions for both cases are shown in FIGS. 13A-13B—FIG. 13A being an enhanced reconstruction of FIG. 12A, and FIG. 13B being an enhanced reconstruction of FIG. 12B. The image enhancement algorithm does not use any a priori information about the object 200, and is effectively a deblurring algorithm.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

The invention claimed is:

1. A method of imaging an object using microwave tomography, wherein the method comprises:
   providing one or more antennas positioned relative to an object;
   providing boundary condition apparatus comprising an enclosure and configured to change one or more of the orientation, shape, and volume of the enclosure to present a plurality of different boundary conditions relative to the one or more antennas;
   delivering electromagnetic energy using at least one of the one or more antennas to irradiate the object resulting in scattered electromagnetic energy for each of the plurality of different boundary conditions presented by the boundary condition apparatus;
   sampling the scattered electromagnetic energy using at least one of the one or more antennas for each of the plurality of different boundary conditions; and
   reconstructing an image of the object based on the sampled scattered electromagnetic energy.

2. The method of claim 1, wherein each antenna of the one or more antennas is in a fixed position relative to the object.

3. The method of claim 1, wherein at least one antenna of the one or more antennas is attached to the object.

4. The method of claim 1, wherein delivering electromagnetic energy using at least one of the one or more antennas to irradiate the object for each of the plurality of different boundary conditions presented by the boundary condition apparatus comprises delivering electromagnetic energy with each of the one or more antennas individually until each antenna has individually delivered electromagnetic energy to irradiate the object for each of the plurality of different boundary conditions.

5. The method of claim 1, wherein the enclosure is a conductive enclosure, wherein the method further comprises positioning the object within the conductive enclosure.

6. The method of claim 1, wherein the boundary condition apparatus presents each of the different boundary conditions by rotating the enclosure relative to the object and the one or more antennas.

7. The method of claim 1, wherein the one or more antennas comprise less than eight antennas, and wherein the plurality of different boundary conditions comprises at least three different boundary conditions.

8. The method of claim 1, wherein the method further comprises surrounding the object with a low-loss fluid.

9. A system for use in imaging an object comprising:
   one or more antennas positionable relative to an object to be imaged;
   boundary condition apparatus comprising an enclosure and configured to change one or more of the orientation, shape, and volume of the enclosure to present a plurality of different boundary conditions relative to the one or more antennas;
   wherein the one or more antennas are configured to deliver electromagnetic energy to irradiate an object to be imaged resulting in scattered electromagnetic energy for each of the plurality of different boundary conditions, and wherein the one or more antennas are further configured to sample the scattered electromagnetic energy for each of the plurality of different boundary conditions; and
   processing apparatus configured to reconstruct an image of an object based on the sampled scattered electromagnetic energy.

10. The system of claim 9, wherein each antenna of the one or more antennas is in a fixed position relative to the object.

11. The system of claim 9, wherein each antenna of the one or more antennas is configured to be attached to the object.

12. The system of claim 9, wherein the one or more antennas are configured to deliver electromagnetic energy with each of the one or more antennas individually until each antenna has individually delivered electromagnetic energy to irradiate the object for each of the plurality of different boundary conditions.

13. The system of claim 9, wherein the enclosure is a conductive enclosure.

14. The system of claim 9, wherein the boundary condition apparatus presents each of the plurality of different boundary conditions by rotating the enclosure relative to the object and the one or more antennas.

15. The system of claim 9, wherein the one or more antennas comprise less than eight antennas and the plurality of different boundary conditions comprises at least three different boundary conditions.

16. The system of claim 9, wherein the boundary condition apparatus is further configured to surround the object with a low-loss fluid.

17. A method of imaging an object using microwave tomography, wherein the method comprises:

providing one or more antennas positioned relative to an object to be imaged, wherein each of the one or more antennas is in a fixed position relative to the object;

providing an enclosure around the object and changing one or more of the orientation, shape, and volume of the enclosure to present a plurality of different boundary conditions relative to the object being imaged and the one or more antennas;

delivering electromagnetic energy using at least one of the one or more antennas to irradiate the object resulting in scattered electromagnetic energy for each of the plurality of different boundary conditions;

sampling the scattered electromagnetic energy using at least one of the one or more antennas; and reconstructing an image of the object based on the sampled scattered electromagnetic energy.

18. The method of claim 17, wherein the enclosure is a conductive enclosure, wherein changing one or more of the orientation, shape, and volume of the enclosure comprises:

positioning the object within the conductive enclosure; and rotating the conductive enclosure relative to the object and the one or more antennas to a different position for each of the plurality of different boundary conditions.

19. The method of claim 17, wherein the enclosure is triangular.

20. The method of claim 17, wherein the method further comprises surrounding the object with a low-loss fluid.

\* \* \* \* \*